(12) United States Patent
Frincke et al.

(10) Patent No.: US 8,486,926 B2
(45) Date of Patent: Jul. 16, 2013

(54) STEROID TETROL SOLID STATE FORMS

(75) Inventors: James Frincke, San Diego, CA (US); Marvin Lewbart, Voorhess, NJ (US); Christopher Reading, San Diego, CA (US)

(73) Assignee: Harbor Therapeutics, Inc., San Diego, CA (US)

( * ) Notice: Subject to any disclaimer, the term of this patent is extended or adjusted under 35 U.S.C. 154(b) by 785 days.

(21) Appl. No.: 12/272,767

(22) Filed: Nov. 17, 2008

(65) Prior Publication Data

US 2009/0143349 A1   Jun. 4, 2009

Related U.S. Application Data

(63) Continuation-in-part of application No. 11/942,689, filed on Nov. 19, 2007, and a continuation-in-part of application No. 11/941,936, filed on Nov. 17, 2007, now Pat. No. 8,354,396.

(60) Provisional application No. 60/866,395, filed on Nov. 17, 2006, provisional application No. 60/866,700, filed on Nov. 21, 2006, provisional application No. 60/868,042, filed on Nov. 30, 2006, provisional application No. 60/885,003, filed on Jan. 15, 2007, provisional application No. 60/888,058, filed on Feb. 2, 2007.

(51) Int. Cl.
*A61K 31/33* (2006.01)

(52) U.S. Cl.
USPC .......................................................... 514/183

(58) Field of Classification Search
USPC .......................................................... 514/183
See application file for complete search history.

(56) References Cited

U.S. PATENT DOCUMENTS

| | | | |
|---|---|---|---|
| 4,898,694 A | 2/1990 | Schwartz et al. | |
| 5,028,631 A | 7/1991 | Schwartz et al. | |
| 5,206,008 A | 4/1993 | Loria | |
| 5,292,730 A | 3/1994 | Lardy | |
| 5,296,481 A | 3/1994 | Partridge et al. | |
| 5,372,996 A | 12/1994 | Labrie | |
| 5,387,583 A | 2/1995 | Loria | |
| 5,424,463 A | 6/1995 | Lardy et al. | |
| 5,461,042 A | 10/1995 | Loria | |
| 5,506,223 A | 4/1996 | Lardy et al. | |
| 5,593,981 A | 1/1997 | Labrie | |
| 5,763,433 A | 6/1998 | Morfin | |
| 5,859,000 A | 1/1999 | Dowell et al. | |
| 5,912,240 A | 6/1999 | Loria | |
| 6,110,906 A | 8/2000 | Labrie et al. | |
| 6,451,340 B1 | 9/2002 | Arimilli | |
| 6,667,299 B1 | 12/2003 | Ahlem et al. | |
| 7,045,513 B1 | 5/2006 | Parasranpuria et al. | |
| 7,282,505 B2 | 10/2007 | Zhu et al. | |
| 7,462,610 B2 | 12/2008 | Lardy et al. | |
| 7,482,334 B2 | 1/2009 | Frincke et al. | |
| 7,524,835 B2 | 4/2009 | Frincke | |
| 7,659,405 B2 | 2/2010 | Bauer et al. | |
| 7,696,189 B1 | 4/2010 | Frincke | |
| 7,776,845 B2 | 8/2010 | Frincke | |
| 7,842,680 B2 | 11/2010 | Lardy et al. | |
| 7,863,261 B2 | 1/2011 | Frincke | |
| 7,867,990 B2 | 1/2011 | Schultz et al. | |
| 7,910,573 B2 | 3/2011 | Beckmann et al. | |
| 7,910,755 B2 | 3/2011 | Frincke | |
| 7,964,604 B2 | 6/2011 | Eijgendaal et al. | |
| 8,003,636 B2 | 8/2011 | Wollmann et al. | |
| 2003/0060425 A1 | 3/2003 | Ahlem et al. | |
| 2004/0097475 A1 | 5/2004 | Wuts | |
| 2004/0116359 A1 | 6/2004 | Ahlem et al. | |
| 2005/0159366 A1* | 7/2005 | Ahlem et al. | .................. 514/26 |
| 2006/0079492 A1 | 4/2006 | Ahlem et al. | |
| 2006/0088473 A1 | 4/2006 | Dowding et al. | |
| 2006/0211059 A1 | 9/2006 | Taneja | |
| 2007/0014719 A1 | 1/2007 | Reading et al. | |
| 2007/0129282 A1 | 6/2007 | Ahlem et al. | |
| 2008/0015174 A1 | 1/2008 | Reading et al. | |
| 2008/0146532 A1 | 6/2008 | Flores-Riveros et al. | |
| 2008/0153792 A1 | 6/2008 | Frincke et al. | |
| 2008/0153797 A1 | 6/2008 | Frincke et al. | |
| 2008/0221074 A1 | 9/2008 | Flores-Riveros et al. | |
| 2010/0222315 A1 | 9/2010 | Reading et al. | |
| 2010/0227841 A1 | 9/2010 | Stickney et al. | |

FOREIGN PATENT DOCUMENTS

| | | |
|---|---|---|
| AU | 2005/211675 | 10/2005 |
| EP | 1 422 234 | 5/2004 |
| WO | WO 95/10527 | 4/1995 |
| WO | WO 97/17922 | 5/1997 |
| WO | WO 01/30802 | 5/2001 |
| WO | WO 02/069977 | 9/2002 |
| WO | WO 2004/019953 | 3/2004 |
| WO | WO 2008/039566 | 4/2008 |

OTHER PUBLICATIONS

Wang et al, Amelioration of glucose intolerance by the synthetic androstene HE3286: link to inflammatory pathways, *J. Pharmacol. Exp. Ther.*, 333(1):70-80 2010.

Ahlem et al, HE3286: a novel synthetic steroid as an oral treatment for autoimmune disease, *Ann. N.Y. Acad. Sci.*, 1173:781-790 2009.

Auci et al, A new orally bioavailable synthetic androstene inhibits collagen-induced arthritis in the mouse, *Ann. N.Y. Acad. Sci.*, 1110:630-640 2007.

Chinn et al, 3-(16β,17β-dihydroxy-3-oxoandrost-4-en-17α-yl) propionic acid gamma-lactone, its preparation and antimineralocorticoid activity, *J. Med. Chem.*, 16(7):839-843 1973.

*Ex parte Grawe*, Appeal No. 2009-14303, U.S. Appl. No. 10/296,463 (non-precedential).

(Continued)

*Primary Examiner* — Brandon Fetterolf
*Assistant Examiner* — Christopher R Stone
(74) *Attorney, Agent, or Firm* — Angelo Castellino

(57) ABSTRACT

The invention relates to solid state forms of androst-5-ene-3β,7β,16α,17β-triol, formulations containing or prepared from such solid state forms and use of such materials for modulating acute and chronic non-productive inflammation. The formulations can be used to prevent, treat or slow the progression of conditions related to autoimmunity such as arthritis, multiple sclerosis, ulcerative colitis or Type 1 diabetes. The formulations can also be used to prevent, treat or slow the progression of conditions related to metabolic disorders such as Type 2 diabetes.

11 Claims, 3 Drawing Sheets

OTHER PUBLICATIONS

*Ex parte Bush*, Appeal No. 2009-010640 U.S. Appl. No. 10/520,360 (non-precedential).

*Ex parte Zimmerman*, Appeal No. 2003-0919, U.S. Appl. No. 09/463,097 (non-precedential).

Starrett, J. et al. (1994) "Synthesis, Oral Bioavailability Determination, and in vitro Evaluation of Prodrugs of the Antiviral Agent 9-[2-(Phosphonomethoxy)ethyl]adenine (PMEA)" J. Med. Chem. 37: 1857-64.

* cited by examiner

STEROID TETROL SOLID STATE FORMS

CROSS REFERENCE TO RELATED APPLICATIONS

This nonprovisional U.S. patent application is a continuation-in-part of and claims priority under 35 USC 120 from pending U.S. non-provisional application Ser. No. 11/942,689, filed on Nov. 19, 2007 and from pending U.S. non-provisional application Ser. No. 11/941,936, filed Nov. 17, 2007, which claims priority under 35 USC 119(e) from U.S. provisional application Ser. No. 60/866,395, filed Nov. 17, 2006, U.S. provisional application Ser. No. 60/866,700, filed Nov. 21, 2006, U.S. provisional application Ser. No. 60/868,042, filed Nov. 30, 2006, U.S. provisional application Ser. No. 60/885,003, filed Jan. 15, 2007, and U.S. provisional application Ser. No. 60/888,058, filed Feb. 2, 2007, all of which are incorporated herein by reference.

FIELD OF THE INVENTION

The invention relates to solid state forms of androst-5-ene-3β,7β,16α,17β-tetrol, formulations containing or prepared from such solid state forms and use of such materials for modulating inflammation, metabolic disorders and other conditions described herein. The formulations can be used to treat or slow the progression of autoimmune conditions such as arthritis, multiple sclerosis or ulcerative colitis.

BACKGROUND OF THE INVENTION

The ability of a substance to exist in more than one crystalline form is defined as polymorphism and these different crystalline forms are named "polymorphs". In general, polymorphism is caused by the ability of the molecule of a substance to change its conformation or to form different intermolecular and intramolecular interactions giving different atom arrangements that is reflected in the crystal lattices of different polymorphs. However, polymorphism is not a universal feature of solids, since some molecules can exist in one or more crystal forms while other molecules cannot. Therefore, prediction of polymorphism remains a highly unpredictable art.

The different polymorphs of a substance posses different energies of the crystal lattice and thus each polymorph typically shows one or more different physical properties in the solid state, such as density, melting point, color, stability, dissolution rate, flowability, compatibility with milling, granulation and compacting and/or uniformity of distribution (See, e.g., P. DiMartino, et al., *J. Thermal Anal.* 48:447 458 (1997)). The capacity of any given compound to occur in one or more crystalline forms (i.e. polymorphs) is unpredictable as are the physical properties of any single crystalline form. Different physical properties of a substance may affect the ability to prepare different pharmaceutical formulations comprising the substance and may also affect the stability, dissolution and bioavailability of a solid-state formulation, which subsequently affects suitability or efficacy of such formulations in treating disease.

Therefore, knowledge of polymorphism of a compound for use in preparing a composition, such as a pharmaceutically acceptable formulation to treat a disease in a subject, can sometimes affect the development of a medicament. On the basis of this knowledge, an individual polymorph having one or more desirable properties can be selected for the development of a pharmaceutical formulation having the desired property(ies).

In the case of a chemical substance that exists in more than one polymorphic or pseudo-polymorphic form, a less thermodynamically stable form can occasionally convert to the more thermodynamically stable form at a given temperature after a sufficient period of time. When this transformation is not rapid, such a thermodynamically unstable form is referred to as a "metastable" form. In some instances, the stable form exhibits the highest melting point, the lowest solubility, and the maximum chemical stability. In other cases, the metastable form may exhibit sufficient chemical and physical stability under normal storage conditions to permit its use in a commercial form. In this case, the metastable form, although less thermodynamically stable, may exhibit properties desirable over those of the stable form, such as enhanced solubility or better oral bioavailability. Likewise a non-crystalline material may have enhanced solubility in comparison to its crystalline forms due to reduction or absence of crystal lattice forces that must be overcome to effect dissolution of these materials.

SUMMARY OF THE INVENTION

Figure 1:
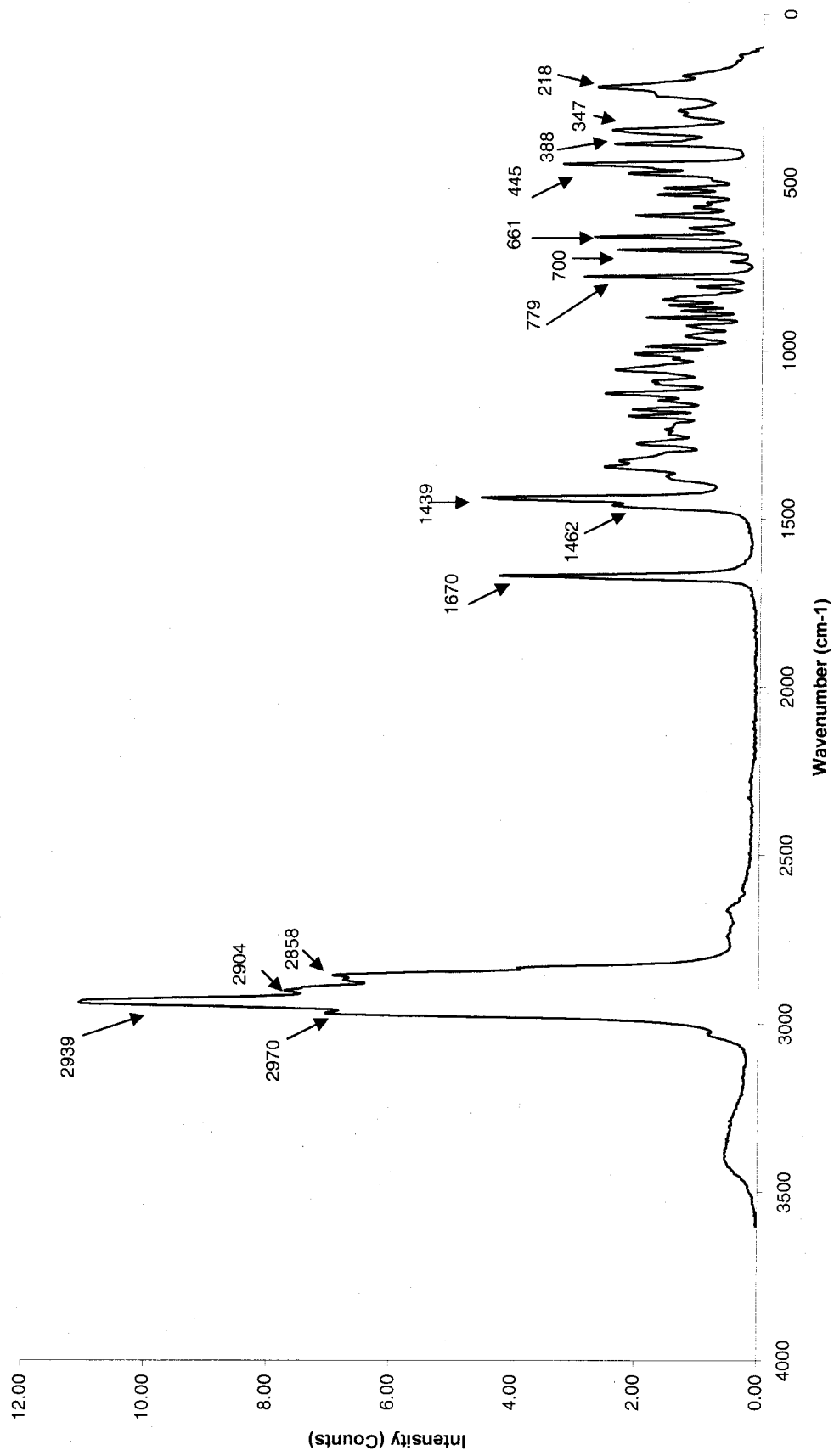
FIG. 1. Solid phase Raman Spectrum of a solid state form of androst-5-ene-3β,7β,16α,17β-tetrol FIG. 2. X-Ray powder diffraction pattern of a solid state form of androst-5-ene-3β,7β,16α,17β-tetrol FIG. 3. Differential Thermal and Thermal Graviometric Traces of a solid state form of androst-5-ene-3β,7β,16α,17β-tetrol

The invention compounds, compositions, formulations or methods accomplish one or more of the following objects. One object is to provide a solid state form of a formula 1 compound (F1C) having the structure

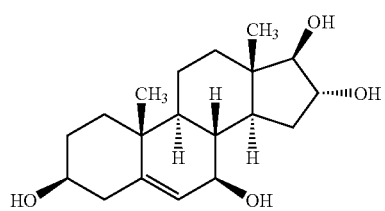

The Formula 1 compound (hereafter also referred to as Compound 1, androst-5-ene-3β,7β,16α,17β-tetrol or 3β,7β,6α,17β-tetrahydroxy-androst-5-ene) has been prepared in solid state form.

One embodiment of the invention is directed to a particular solid state form of Compound 1 substantially free of other crystalline or solid state forms of Compound 1.

Another embodiment of the invention is directed to methods to prepare Compound 1 in solid state form.

Other embodiments of the invention are directed to methods of preparation of a particular solid state form of Compound 1 disclosed herein Other embodiments of the invention are directed to invention compositions and formulations comprising a solid state form of Compound 1 that is substantially free of other solid state and non-solid state forms of Compound 1 and methods for preparation of the invention compositions and formulations.

Other embodiments of the invention are directed to solid invention compositions or formulations comprising a solid state form of Compound 1 and methods for preparation of the solid formulations.

Still other embodiments of the invention are directed to liquid formulations or invention compositions prepared by contacting or admixing a solid state form of Compound 1 with a liquid excipient, optionally in the presence of another excipient, and methods for preparation of the liquid formulation.

Other invention objects include methods of treating one or more symptoms of a pathological condition associated with acute or chronic, non-productive inflammation using a solid state form of androst-5-ene-3β,7β,16α,17β-tetrol or an invention composition or formulation comprising the solid state form.

Other invention objects include methods of treating one or more symptoms of a pathological condition associated with a metabolic condition or disease including type 2 diabetes, obesity, insulin resistance, hyperglycemia, impaired glucose utilization or tolerance, impaired or reduced insulin synthesis, a hyperlipidemia condition such as hypercholesterolemia, hypertriglyceridemia or elevated free fatty acids and hypolipidemia conditions.

Other invention objects provide for treatment methods for autoimmune diseases, lung inflammation conditions, inflammatory bowel diseases, metabolic and cardiovascular conditions, neurodegenerative diseases and hyperproliferation conditions by using an effective amount of a solid state form of Compound 1 or by administering a formulation comprising a solid state form of Compound 1 to a subject having such a disease or condition.

Thus, the solid state form of Compound 1 described herein, or solid or liquid invention compositions or formulations derived from this solid state form, are useful to treat or slow the progression of a number of clinical conditions that are associated with acute inflammation, chronic inflammation or tissue damage, which may be acute or chronic.

The chronic conditions to be treated due to or resulting from acute or chronic, non-productive inflammation are typically progressive and worsen over a period of months or years. These clinical conditions include autoimmune diseases, e.g., a lupus condition such as systemic lupus erythematosus or discoid lupus, arthritis conditions such as rheumatoid arthritis or osteoarthritis, multiple sclerosis and an inflammatory bowel disease such as ulcerative colitis or Crohn's disease (regional enteritis).

Other chronic conditions to be treated due to or resulting from chronic, non-productive inflammation include chronic lung conditions such as a chronic obstructive pulmonary disease (COPD), acute asthma, chronic asthma, emphysema, acute bronchitis, allergic bronchitis, chronic bronchitis and fibrosing alveolitis (lung fibrosis) conditions, e.g., subepithelial fibrosis in patients having chronic bronchitis, asthma and/or COPD.

Additional clinical conditions to be treated having a chronic inflammatory component include hyperglycemia, diabetes, liver cirrhosis conditions, nonalcoholic steatohepatitis (NASH), fatty liver conditions or other metabolic diseases resulting from or propagated by chronic, non-productive inflammation.

Still other clinical conditions to be treated having a chronic inflammatory component also include hyperproliferation conditions such as a hormone associated cancer or hormone sensitive cancer including ovarian cancer, endometrial cancer, prostate cancer or breast cancer or a hyperplasia such as benign prostatic hyperplasia.

The solid state form of androst-5-ene-3β,7β,16α,17β-tetrol (i.e., Compound 1) described herein, or solid or liquid formulations or invention compositions derived from this solid state form are also useful to treat or slow the progression of neurodegenerative conditions, bone loss or bone damage conditions and traumas including Alzheimer's disease, Parkinson's disease, dementias, a cognitive impairment condition without dementia, stroke and other central nervous system ischemia conditions, hemorrhage, thromboembolism, brain trauma, myocardial infarction, chemical or thermal burns, an osteoporosis condition such as postmenopausal osteoporosis, idiopathic osteoporosis or osteoporosis associated with a glucocorticoid treatment (e.g., dexamethasone, prednisone, cortisone, corticosterone, etc.), bone fractures and skin lesions or disruptions, e.g., associated with wounds, keratosis or psoriasis.

Invention embodiments include a dietary supplement product or nutraceutical product that comprises or contains (1) androst-5-ene-3β,7β,16α,17β-tetrol, usually the solid state form of androst-5-ene-3β,7β,16α,17β-tetrol described herein Other embodiments and advantages of the present invention are described further in the following detailed description. The claimed agents and methods are also useful to reduce one or more symptoms associated with the conditions described herein. Additionally, the use of the agents and methods described herein can be combined with one or more conventional treatments for each of these disorders.

DETAILED DESCRIPTION

Definitions

As used herein and unless otherwise stated or implied by context, terms that are used herein have the meanings that are defined here. The descriptions of embodiments and examples that are described illustrate the invention and they are not intended to limit it in any way. Unless otherwise contraindicated or implied, e.g., by including mutually exclusive elements or options, in these definitions and throughout this specification, the terms "a" and "an" mean one or more and the term "or" means and/or.

The phrase "metabolic disorder" or "metabolic disease" means one or more conditions such as type 1 diabetes, type 2 diabetes, obesity, insulin resistance, hyperglycemia, impaired glucose utilization or tolerance, impaired or reduced insulin synthesis, a hyperlipidemia condition such as hypercholesterolemia, hypertriglyceridemia or elevated free fatty acids and hypolipidemia conditions. Hypercholesterolemias include hyper-LDL cholesterolemia or elevated LDL cholesterol. Hypolipidemias include hypo-HDL cholesterolemia or low HDL cholesterol levels. Type 1 diabetes includes Immune-Mediated Diabetes Mellitus and Idiopathic Diabetes Mellitus. Type 2 diabetes includes forms with predominant or profound insulin resistance, predominant insulin deficiency and some insulin resistance and forms intermediate between these.

An "invention formulation" or "formulation" as used herein is a composition, comprised of or prepared from a blend of solid state androst-5-ene-3β,7β,16α,17β-tetrol and one or more excipients typically two, three or more excipients, wherein the composition can be administered to a subject without further manipulations that change the number or identity of the formulation ingredients or ingredient proportions that are present immediately prior to the manipulation. The formulation may be comprised of or be prepared from a solid state form of androst-5-ene-3β,7β,16α,17β-tetrol (e.g., the solid state form prepared according to the procedure described herein).

An "invention composition" is a composition that is an intermediate one can use to make the invention formulations, i.e., a change(s) in an ingredient(s) or its amount(s) is needed to make a formulation. Thus, invention compositions include compositions where further processing is required before it is a formulation, e.g., by mixing or adding a desired amount of an ingredient such as a diluent (e.g. vehicle) as in reconstitution of a lyophilized solution.

"Solid State" as used herein refers to a physical state of Compound 1 wherein the majority of the mass of Compound 1 that is present exists as a solid and includes solid state forms such as a single polymorph form of Compound 1, a single pseudo-polymorph form of Compound 1, a mixture of two or more, typically two or three, polymorph or pseudo-polymorph forms of Compound 1 or a combination of any one of these solid state forms with non-solid or non-crystalline Compound 1.

"Solid state formulation" or "solid formulation" as used herein refers to a formulation comprising a solid state form of Compound 1 and one or more pharmaceutically acceptable excipients wherein the majority of the mass amount of the solid state form of Compound 1 remains in that solid state form when admixed with the excipients in proportions required for the solid state formulation. Dosage units containing a solid state formulation include tablets, capsules, ampoules, suspensions and other dosage units typically associated with parenteral or enteral administration of an active pharmaceutical ingredient to a subject in need thereof in solid state form.

"Liquid formulation" as used herein refers to a formulation wherein a solid state form of Compound 1 has been admixed or contacted with one or more excipients, wherein at least one of the excipients is in liquid or non-solid state form (i.e., a non-solid excipient), in proportions required for the liquid formulation, such that a majority of the mass amount of Compound 1 is dissolved into the non-solid excipient(s). Dosage units containing a liquid formulation include syrups, gels, ointments and other dosage units typically associated with parenteral or enteral administration of an active pharmaceutical ingredient to a subject in need thereof in non-solid state form.

"Parenteral administration" as used here means introduction of a pharmacologically active compound, composition or formulation to a subject through a route other than the digestive system and includes injection dependent routes such as intravenous (i.v.), subcutaneous (s.c.), intradermal, epidural, intraperitoneal, intramuscular (i.m.), intramedullary, intraorbital, intracapsular, intraspinal, intrathecal or intrasternal and injection independent routes such as topical, intranasal, ophthalmic or inhalation. Preferred routes of parenteral administration are i.v., s.c., i.m. and intradermal.

"Pharmaceutically acceptable" as used herein in reference to the different composition or formulation components, or the composition or formulation itself, means that the components of the composition or formulation itself do not cause unacceptable adverse side effects in relation to the condition and the subject being treated. Examples of pharmaceutically acceptable components are provided in United States Pharmacopoeia and National Formulary, USP 30-NF 25, May 2007.

"Parenteral composition" or "parenteral formulation" as used here means an invention composition or formulation, comprising or prepared from a solid state form of Compound 1, suitable for use in parenteral administration to a subject in need thereof. Pharmaceutically acceptable invention compositions or formulations suitable for use in parenteral administration in human or veterinary applications include, by way of example and not limitation, dry powders, liquid solutions, suspensions, emulsions, gels, creams, intramammary infusions, intravaginal delivery systems and implants.

An "excipient", "carrier", "pharmaceutically acceptable carrier" or similar terms mean one or more component(s) or ingredient(s) means a component or an ingredient, other than the active pharmaceutical ingredient (i.e. Compound 1), that is included in a invention composition or formulation and has been found acceptable in the sense of being compatible with the other ingredients of the invention compositions or formulations and has been appropriately evaluated for safety and found not overly deleterious to the patient or animal to which the invention composition or formulation is to be administered. Excipients typically used in the pharmaceutical formulation arts include diluents, disintegrants, binders, anti-adherents, lubricants, glidants, sorbents, suspension agents, dispersion agents, wetting agents, surface-active agents, flocculating agents, buffering agents, tonicity-adjusting agents, metal chelator agents, anti-oxidants, preservatives, fillers, flow enhancers, compression aids, colors, sweeteners, film formers, film coatings, favors and printing inks. Any solid excipient may exist as a fine powder or granulated solid. Excipients, as used herein, may optionally exclude one or more excipients that are inconsistent for use in a contemplated route of administration and usually include one or more components typically used in the pharmaceutical formulation arts, e.g., one, two or more of fillers, binders, disintegrants, dispersants, preservatives, glidants, surfactants and lubricants. Exemplary excipients include povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride and saccharides such as mannitol, glucose, fructose, sucrose or lactose.

A "suspension" as used here unless specified or implied by context is suspended as a finely divided solid in a liquid carrier (vehicle) at a time prior to administration. The suspension may be either ready to use or a dry powder reconstituted as a suspension dosage form just prior to use. Suspensions are used when Compound 1 is insoluble or poorly soluble in a desired diluent or vehicle or has insufficient solubility in the desired diluent volume to be used for a unit dosage form and will typically include a suspending and a wetting agent, if the suspending agent that is present does not already serve this purpose. Typically, a suspension will also include a buffering agent and a preservative. In a colloidal suspension, the particles of Compound 1 are typically about less than about 1 μm in size. In a coarse suspension, they are larger than about 1 μm or larger than about 5 μm in average particle size. The practical upper limit for individual particles of Compound 1 in coarse suspensions is about 50 μm to 75 μm although particles up to 200 μm may be suitable. Design consideration for developing a suspension for parenteral administration are given in Akers, et al. *J. Parenteral Sci. Tech.* 41: 88-96 (1987); Nash, R A "Suspensions" in Encyclopedia of Pharmaceutical Technology $2^{nd}$ ed. Taylor and Francis, 2006, pp 3597-3610.

A "surface-active agent" (surfactant) is a substance, which, at low concentrations, interacts between the surfaces a solid and a fluid in which the solid has insufficient solubility. Surface-active agents are amphipathic in structure having both polar (hydrophilic) and non-polar (hydrophobic) regions in the same molecule. The fluid may be a liquid excipient present in a suspension formulation comprising a solid state form of Compound 1 and the liquid excipient. Alternatively, the surface active agent may be present in an oral solid dosage form comprising a polymorph or pseudo-polymorph of Compound 1 or a mixture thereof and the surface active agent. Examples of surface active agents used in the formulation arts are given in Corrigan, O. I.; Healy, A. M. "Surfactants in Pharmaceutical Products and Systems" in *Encyclopedia of Pharmaceutical Technology* $2^{nd}$ ed. Taylor and Francis, 2006, pp 3583-3596.

A "suspending agent" as used here is a substance that facilitates and maintains the physical stability of a suspension by adjusting the viscosity of the liquid component and to more closely match the density of this component with the density of the particles in the suspension such that sedimentation or separation is retarded. Non-limiting examples of suspending agents suitable for parenteral administration include cellulose and derivatives thereof, such as sodium carboxymethylcellulose (CMC), methylcellulose microcrystalline cellulose, and dextran and derivatives thereof, gums, clays and gelatin. For injection dependent routes of administration of suspensions, CMC or gelatin are typically used. Considerations for choice of a suitable suspending agent include resuspendability of the drug in the diluent or vehicle to permit homogeneous dosing when withdrawing the suspension from its container or packaging system, avoidance of a physically instability (e.g. hard caking), syringeability, which is defined as the ability to withdraw a homogeneous dose of the composition or formulation from its container or packaging system and injectability, which is defined as the ability to eject the composition or formulation through the needle used to administer the composition or formulation to a subject.

A "wetting agent" as used herein is a surfactant and permits interaction between particles of Compound 1 and a diluent to provide an evenly distributed suspension to improve the rate of dissolution of the particles into a vehicle for preparation of a liquid formulation or in gastric fluid when ingested to improve oral bioavailability.

A "diluent", as used here, typically includes a non-aqueous liquid, such as benzyl benzoate, cottonseed oil, N,N-dimethylacetamide, a $C_{2-12}$ alcohol (e.g., ethanol), glycerol, peanut oil, propylene glycol, a polyethylene glycol ("PEG"), vitamin E, poppy seed oil, propylene glycol, safflower oil, sesame oil, soybean oil and vegetable oil or an aqueous liquid, such as WFI (water for injection) or D5W (5% dextrose in water for injection) and may include one or more other excipients such as buffers, chelating agents and preservatives.

A "vehicle" as used here is a diluent that comprises the majority of the total volume or mass of an invention composition or formulation to be administered.

"Aqueous-based" as used here means a diluent, vehicle, solution, composition or formulation so described wherein the major component by volume is water.

"Substantially pure" as used herein refers to a solid state form of Compound 1 that contain less than about 3% or less or than about 2% by weight total impurities and less than about 0.5% by weight residual organic solvent or other impurities such as decomposition or synthesis by-products.

"Substantially identical" as used herein refers to data traces that are comparable in peak position and amplitude or intensity with variations typically due to sample positioning or handling or the identity of the instrument employed to acquire the traces or other variations or fluctuations normally encountered within or between laboratory environments. With respect to XRPD traces, "substantially identical" takes into account variations in XRPD peak intensity, noise, line broadening and presence of extraneous peaks. Such variations may be attributable to differing amounts of crystal defects that may arise, e.g., form slight variations in the example procedures disclosed herein for preparing the solid state form of Compound 1, variations in grinding or other mechanical procedures or differences in particle size or particle size distribution. Other variations may arise from e.g., sample mounting when there is a preferred orientation, or positioning outside the focal plane of the X-ray beam. One quantitative method that may be used to determine if XRPD spectra are substantially identical is hierarchical cluster analysis as described in US Pat. Pub. No. 2004/0103130, which is incorporated by reference into the present disclosure.

"Essentially free" as used herein refers to a component so identified as not being present in an amount that would adversely affect the desired properties of an invention composition or formulation in which the component may be found. For example, "essentially free of liquid" means an invention composition or formulation in solid form that does not contain water or solvent, in liquid form, in an amount that would adversely affect the pharmaceutical acceptability of the formulation or composition for use in, or preparation of, a solid dosage form. In a suspension formulation as the solid dosage form, liquid excipient(s) comprising the suspension formulation are not included within this definition.

"Substantially free" as used herein refers to a solid state form of Compound 1 wherein more than about 60% by weight, usually at least about 80% by weight or more typically at least about 90% by weight of Compound 1 is present as the given solid state form or is essentially free of one or more other solid forms of Compound 1. For example, the term "a pseudo-polymorph of Compound 1 substantially free of" another solid form refers to a solid form of Compound 1 wherein more than about 60% of Compound 1 is present as the specified pseudo-polymorph. Such compositions typically contain at least about 80%, usually at least about 90%, of the specified pseudo-polymorph with the remaining present as non-solid Compound 1 or other solid state forms of Compound 1 not including the specified pseudo-polymorph. When the defined solid state form is a mixture of one or more polymorph or pseudopolymorph forms of Compound 1 the term "a solid state form of Compound 1 substantially free of" another solid state form refers to a solid form of Compound 1 wherein more than about 60%, typically at least about 80%, usually at least about 90% of Compound 1 is in the specified solid mixture with remaining Compound 1 present as non-solid Compound 1 or other solid state forms not including the solid forms of the specified mixture. Invention compositions and formulations described herein will typically contain about 90-99% of the defined solid state form of Compound 1, with about 97%, about 98% or about 99% usually preferred.

"Effective amount" as used herein in a content of describing an amount of an excipient means an amount of an excipient that will provide the desired property or properties of the excipient without interfering to a measurable extent the desired pharmacological properties of the active pharmaceutical ingredient or other excipients in a composition or formulation.

"Therapeutically effective amount" as used here is an amount of an invention composition or formulation that contains a sufficient amount of androst-5-ene-3β,7β,16α,17β- tetrol (i.e., Compound 1) for treating a specified condition or disease. Typically, the amount of Compound 1 in the invention composition or formulation exhibits acceptable toxicity in relation to the condition being treated but has sufficient efficacy as contained within the composition or formulation to elicit the desired therapeutic effect after administration of the composition or formulation to a subject through an intended route of administration. When describing a solid state form or a mixture of two or more forms of Compound 1, wherein at least one form is a solid state form, "therapeutically effective amount" means an amount of Compound 1 comprised of or prepared from the solid state form or the mixture of forms that is sufficient to elicit a desired response, e.g., detectable restoration of normal physiological condition in a subject to which it is administered such as a decrease or stabilization of a symptom of the condition or disease being treated or a detectable change in a biomarker indicative of the expected biological response or to detectable modulation or amelioration of a cellular parameter. An effective amount may be a single dose or two or more subdoses of Compound 1 in a formulation comprised of or prepared from a solid state or a mixture of two or more solid state forms of Compound 1 administered in one day, or it may be administered as multiple doses over a period of time, e.g., over 2 days to about 1, 2, 3, 4 or 5 years. The effective amount may also be administered in multiple treatment cycles as typically done in administration of cytotoxic agents for the treatment of cancer. The treatment cycles may be separated by one or more days or weeks, typically 1-2 weeks or may be separated by a longer period of time if remission of the hyperproliferation condition is achieved whereupon treatment is reinstituted upon recurrence of the condition. Treatment cycles include daily administration of Compound 1 for 2 weeks, 4 weeks or 12 weeks.

Terms such as "use", "treat" or "treatment" or the like in the context of using an invention composition or formulation in treatment methods or other methods disclosed herein means that an invention composition or formulation is used to administer to a subject, deliver to the subject's tissues or contact with tissues, cells or cell free systems, (e.g., as described herein) Compound 1. Typically a treatment results in at least a transient reduction or frequency of a symptom, eliminating a symptom or its underlying cause, preventing the occurrence of a symptom or its underlying cause or improvement or remediation of damage caused by a symptom or a disease condition.

"Administration of formulation comprising or prepared from a solid state form of Compound 1", or "treatment with a formulation comprising or prepared from a solid state form of Compound 1" or similar terms mean that a formulation comprising Compound 1, in the solid state, is administered to, or delivered to, a subject, such as a human, non-human primate, dog or rodent or to the subject's tissues by one or more suitable methods, e.g., by an oral, topical, parenteral, buccal or sublingual route.

"Prevent" or "prevention" of a condition or symptom as used here means that the onset of the condition or symptom can in some subjects be delayed for at least some period of time in at least some treated subjects. "Prevent" or "prevention" can also be viewed as a delay in detectable dissemination of a condition or disease as measured by delayed appearance of symptoms of the condition or disease. Such effects can be apparent in a minority of subjects or in a majority of subjects, which is observed in many clinical treatment situations, e.g., treatments where a treatment can cause a disease or a symptom thereof go into remission and the remission can be permanent or for some period of time, e.g. about 1-3 months, about 4-6 months, about a year or about two to five years. The treatments described here can generate similar effects, which are referred to as preventing or prevention of the condition or the symptom. Thus, "preventing" or "prevention" as used herein has the meaning commonly applied by the medical arts and means taking advance measures against a condition or disease state that is possible or probable or defending against a condition. Therefore, preventing or prevention of a condition does not mean stopping each and every conceivable occurrence of the condition so referenced with absolute certainty or to preclude the possibility of the event from happening in all or a majority of all subjects, although such events may occur.

"Prophylactic" as used herein means defending against a condition or disease and does not mean stopping the occurrence of the condition or disease so referenced under every conceivable circumstance with absolute certainty or to preclude the possibility of the event from happening in all or a majority of all subjects, although such outcomes may occur.

"Subject to developing" as used herein means prone to, at risk of, or tending towards developing a condition so referenced. Thus, "subject to developing" refers to the likelihood of a subject, based upon risk factors predicated on pre-existing health status, family history, behavior, genetic marker(s) or biochemical marker(s) that have been derived from a population of subjects to which the subject belongs, to suffer from a condition so identified. Thus, a subject, such as a human, subject to developing a disease or condition refers to a human subject with a statistically greater likelihood of developing the disease or condition as a result of the human subject possessing one or more of the known risk factors for the disease or condition.

"Ameliorate", "amelioration", "improvement" or the like means a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated using an invention composition or formulation comprising or prepared from Compound 1 in one or more crystalline forms, where the untreated subjects have, or are subject to developing, the same or similar disease, condition, symptom or the like. Amelioration of a disease, condition, symptom or parameter indicative of the severity of the disease, condition or symptom thereof may be determined subjectively or objectively, e.g., self assessment by a subject(s), by a clinician's assessment or by conducting an appropriate assay or measurement, including, e.g., a quality of life assessment as measured, for example, by pain score, a slowed progression of a disease(s) or condition(s), a reduced severity of a disease(s) or condition(s), or a suitable assay(s) for the level or activity(ies) of a biomolecule(s), cell(s) or by detection of cell migration within a subject that is indicative of dissemination of the condition. Amelioration may be transient, prolonged or permanent or it may be variable at relevant times during or after a formulation comprising Compound 1 is administered to a subject or is used in an assay or other method described herein or a cited reference, e.g., within about 1 hour of the administration or use of Compound 1 to about 3, 6, 9 months or more after a subject(s) has received a solid composition or formulation comprising a solid state form of Compound 1 or a liquid formulation prepared from a solid state form of Compound 1. Improvement in a subject is sometimes measured by progression free survival, stabilization or decrease in intensity of a symptom associated with the disease or condition being treated, delayed appearance of new symptoms or improvement in a biomarker level (e.g., decrease in serum level of a pro-inflammatory cytokine) indicative of the desired pharmacological activity.

A "subject" means a human or an animal. Usually the animal is a mammal or vertebrate such as a non-human primate dog or rodent. Subsets of subjects include subjects of a given species or group of species of varying ages, e.g., young humans, e.g., about 1 week of age to about 9 years of age, adolescent humans, e.g., about 10-19 years of age, adult humans, e.g., about 20-100 years of age, and mature adult or elderly humans, e.g., at least about 55 years of age, at least about 60 years of age, at least about 65 years of age or a range of ages such as about 60-100 years of age. Thus, as used herein, prevention or treatment of a disease, condition or symptom thereof may include or exclude any subset of subjects that are grouped by age.

"Condition" or "disease state" as used herein are interchangeable terms and refers to a physiological state in a subject that is not normal or is abnormal in intensity or duration and can be treated or prevented by administration of an invention composition or formulation.

"Polymorph" as used herein refers to a defined crystalline form of Compound 1. Polymorphs typically differ in their physical properties due to the order of the molecules in the lattice of the polymorph. In addition, the physical properties of the polymorph can differ due to the presence of hydrates, solvates or other molecules incorporated into the lattice of the polymorph. Typically, polymorphs are readily distinguished by one or more physical or analytical properties such as rate of dissolution, Infrared and Raman spectroscopy, X-ray diffraction techniques such as crystal and powder diffraction techniques, solid state $^1$H-NMR and thermal techniques such as melting point, differential thermal analysis, differential scanning calorimetry and thermal gravimetric analysis. Polymorphs that exist as hydrates or solvates are referred to as pseudo-polymorphs and represent different solid state forms in view of the same polymorph form that is anhydrous or not a solvate.

"Crystalline form" as used here refers to a polymorph or pseudo-polymorph form of Compound 1, mixtures of such forms or a solid state mixture of one or more polymorph or pseudo-polymorph forms, optionally in the presence of non-crystalline material or non-solid state forms, wherein the polymorph or pseudo-polymorph form or forms contributes the majority of mass to the solid state mixture.

"Hydrate" as used here refers to a pseudo-polymorph form of Compound 1 that contains water molecules as an integral part of the solid state form and does not refer to water that is non-specifically bound to bulk compound. Hydrates can be classified into three categories: 1) isolated site hydrates, 2) channel hydrates and 3) ion associated hydrates. In the crystal structure of an isolated site hydrate the water molecules are isolated from direct contact with other water molecules by Compound 1 molecules, whereas in channel hydrates the water molecules are located next to each other along one direction in the lattice. Hydrates can contain stoichiometric or nonstoichiometric amounts of water molecules per Compound 1 molecule. An expanded channel hydrate can take up water into the channels when exposed to high humidity and release water when exposed to relatively low humidity. The crystal lattice of such hydrates can expand or contract as hydrate formation or dehydration proceeds, changing the dimensions of the unit cell. Typically, water will be present in a stoichiometric hydrate in the ratio of 0.25, 0.5, 1.0, 1.5 or 2.0. Hydrates are usually more stable than their anhydrous counterparts at conditions below its dehydration temperature. Isolated site hydrates usually dehydrate at relatively higher temperatures than channel hydrates. The dehydration process of isolated site hydrates is sometimes destructive for the crystal structure since it usually requires rearrangement of the molecules in the unit cell in order to allow water molecules to escape the lattice.

"Solvate" as used here refers to pseudo-polymorph form of a compound so identified that contains solvent molecules other than water that is combined in a definite ratio to the molecules of the compound and is an integral part of the solid state form and does not refer to solvent that is non-specifically bound to bulk compound. Typically, solvent will be present in a solvate in the ratio of 0.25, 0.5, 1.0, 1.5 or 2.0.

Inflammation Treatments.

An aspect of some claimed embodiments is that the solid state form of androst-5-ene-3β,7β,16α,17β-tetrol (i.e., Compound 1) described herein, or solid or liquid formulations or invention compositions derived from this solid state form, can decrease inflammation by affecting mediators of inflammation such as NF-κB, IL-6 or TNFα. The NF-κB molecule often is an important mediator of inflammation. Increased activation of NF-κB is associated with a range of inflammatory diseases and autoimmune conditions. Anti-inflammatory activity from compounds in vivo could arise, e.g., from eliciting prostaglandin synthesis and other activity in liver, leading to a systemic anti-inflammation response. Alternatively, anti-inflammation activity for compounds could arise from the capacity of the compounds to inhibit stimulation of NF-κB activity that arises from sources other than LPS. A number of different materials can activate NF-κB activity, including LPS, TNF-α, IL-1, the presence of certain viral or bacterial gene products, activation of B-cells or T-cells, or exposure of cells to ultraviolet radiation. Not all cell types can respond to all of these stimuli since not all cells express the signaling machinery that is needed to respond to each of these stimuli. Most cell types can respond to one or a few of these signals, but rarely can a given cell type respond to all.

Compound 1 can be used to treat or ameliorate conditions or symptoms associated with acute or chronic inflammation. Conditions and symptoms include inflammation such as pain, fever or fatigue; endometriosis; fever; fibromyalgia; a myelitis condition such as acute transverse myelitis; glomerulonephritis; graft versus host disease, organ or tissue transplant rejection, e.g., kidney, lung, bone marrow or liver transplant; hemorrhagic shock; fibromyalgia; hyperalgesia; inflammatory bowel disease; gastritis; irritable bowel syndrome; ulcerative colitis; a peptic ulcer; a stress ulcer; a bleeding ulcer; gastric hyperacidity; dyspepsia; gastroparesis; gastroesophageal reflux disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); a demyelinating condition such as multiple sclerosis or progressive multifocal leukoencephalopathy, which may be remitting or relapsing; myopathies (e.g., muscle protein metabolism, especially in sepsis); neurotoxicity (e.g., as induced by HIV); osteoporosis; pain, including cancer-related pain; Parkinson's disease; Alzheimer's disease; periodontal disease; pre-term labor; psoriasis; reperfusion injury; septic shock; side effects from radiation therapy; temporal mandibular joint disease; alcohol-induced liver injury including alcoholic cirrhosis; rheumatic fever; sarcoidosis; scleroderma; chronic fatigue syndrome; coronary conditions and indications, including congestive heart failure, coronary restenosis, myocardial infarction, myocardial dysfunction (e.g., related to sepsis), and coronary artery bypass graft; sleep disturbance; uveitis; seronegative polyarthritis; ankylosing spondylitis; Reiter's syndrome and reactive arthritis; Still's disease; psoriatic arthritis; enteropathic arthritis; polymyositis; dermatomyositis; scleroderma; systemic sclerosis; vasculitis (e.g., Kawasaki's disease); inflammation resulting from, e.g., strain, sprain or cartilage damage; wound healing; thin or fragile skin; petechiae or ecchymoses; erythema; and trauma. Trauma includes wounds, chemical burns, thermal burns, radiation burns and tissue or organ damage associated with a surgery such as an orthopedic surgery or an abdominal surgery. Inflammation conditions can include inflammation associated with reperfusion injury, restenosis after angioplasty, myocardial or cerebral infarction.

Unwanted inflammation conditions or symptoms, include lung inflammation conditions, e.g., cystic fibrosis, acute asthma, chronic asthma, steroid resistant asthma, acute bronchitis, chronic bronchitis, emphysema, psoriasis, eczema, adult respiratory distress syndrome (ARDS) or chronic obstructive pulmonary disease (COPD).

Autoimmune Conditions.

the solid state form of Compound 1 described herein, or solid or liquid invention compositions or formulations derived from this solid state form, can be used to treat, prevent or slow the progression of autoimmune or related conditions such as type 1 diabetes, Crohn's disease, arthritis, contact dermatitis, lupus and multiple sclerosis (MS) conditions. MS conditions include relapsing-remitting MS and secondary progressive MS. The lupus conditions include systemic lupus erythematosus, lupus erythematosus-related arthritis, lupus erythematosus-related skin changes, lupus erythematosus-related hematologic abnormalities, lupus erythematosus-related kidney impairment, lupus erythematosus-related heart or lung disease, lupus erythematosus-related neuropsychiatric changes, lupus erythematosus-related tissue inflammation, discoid lupus erythematosus, subacute cutaneous lupus erythematosus and drug-induced lupus erythematosus. Arthritis and related conditions include rheumatoid arthritis, osteoarthritis, fibromyalgia, primary osteoarthritis, secondary osteoarthritis, psoriatic arthritis, lupus erythematosus-related arthritis, arthritis associated with acute or chronic inflammatory bowel disease or colitis, arthritis associated with ankylosing spondylitis, arthritis-related tissue inflammation, joint pain, joint stiffness, impaired joint movement, joint swelling, joint inflammation and synovium inflammation.

In these claimed embodiments the solid state form of Compound 1 described herein, or solid or liquid invention compositions or formulations derived from this solid state form, can be used to treat, prevent, delay the onset of or slow the progression of conditions such as ankylosing spondylitis, psoriasis, eczema, a dermatitis such as contact dermatitis, a colitis such as ulcerative colitis, Crohn's disease, acute or chronic inflammatory bowel disease, autoimmune renal injury and liver injury. In these embodiments, the solid state form of Compound 1 described herein, or solid or liquid formulations or invention compositions derived from this solid state form can be used in treating lung and airway conditions including asthma conditions such as steroid independent asthma, severe asthma, atopic asthma, acute asthma or chronic asthma, allergic rhinitis, chronic bronchitis, acute bronchitis, cystic fibrosis, emphysema, lung fibrosis, lung airway hyperresponsiveness, chronic obstructive pulmonary disease, pulmonary edema and acute respiratory distress syndrome.

Experimental autoimmune encephalomyelitis (EAE) is an experimental condition in animals that has clinical, histopathological and immunological characteristics similar to human MS and, as with MS, exhibits infiltration into the CNS of T-cells and monocytes. EAE can be induced in susceptible mice by immunization with proteolipid lipoprotein (PLP) in suitable adjuvants. The EAE animal model is an in vivo model of human MS used to study pathogenic mechanisms of MS and to characterize new agents for treating MS.

Treatment of Metabolic Disorders.

In some claimed embodiments, the solid state form of Compound 1 described herein, or solid or liquid invention compositions or formulations derived from this solid state form, are used to treat, prevent or slow the progression of metabolic disorders such as type 1 diabetes, type 2 diabetes, Syndrome X, hypercholesterolemia, hyperglycemia, insulin resistance (e.g., associated with obesity or pre-diabetes), glucose intolerance, hypertriglyceridemia, hyperlipoproteinemia, a lipodystrophy condition, Syndrome X, arteriosclerosis, atherosclerosis and obesity. Syndrome X (including metabolic syndrome) is defined as a collection of two or more abnormalities including hyperinsulemia, obesity, elevated levels of triglycerides, uric acid, fibrinogen, small dense LDL particles and plasminogen activator inhibitor 1 (PAI-1), and decreased levels of HDL-c. Many patients who have insulin resistance but have not yet developed type 2 diabetes are also at a risk of developing metabolic syndrome, also referred to as syndrome X, insulin resistance syndrome or plurimetabolic syndrome. Syndrome-X typically occurs where a patient has two or more of hyperlipidemia, hyperinsulinemia, obesity, insulin resistance, insulin resistance leading to type-2 diabetes and diabetic complications thereof, i.e., diseases in which insulin resistance is the part of the pathophysiology.

Independent risk factors have been associated with cardiovascular disease associated with metabolic disorders can be treated with the F1Cs. These risk factors include hypertension, increased fibrinogen levels, high levels of triglycerides, elevated LDL cholesterol, elevated total cholesterol and low levels of HDL cholesterol. The treatment can result in stimulation of pancreatic β-cells to secrete more insulin and/or a slowed rate of loss of pancreatic β-cells that can occur over time in patients that have diabetes or that are obese.

In these claimed embodiments, treatment of metabolic disorders with the solid state form of Compound 1 described herein, or solid or liquid invention compositions or formulations derived from this solid state form, can be combined with other treatments. Diabetes can be treated with Compound 1 and one or more of a variety of therapeutic agents including insulin sensitizers, such as PPAR-γ agonists such as glitazones; biguanides; protein tyrosine phosphatase-1B inhibitors; dipeptidyl peptidase IV inhibitors; insulin; insulin mimetics; sulfonylureas; meglitinides; α-glucoside hydrolase inhibitors; and α-amylase inhibitors. Metformin, phenformin, acarbose and rosiglitazone are agents that have been used to treat some type of diabetes.

As noted above, claimed embodiments may recite compositions containing the solid state form of Compound 1 described herein to treat, prevent or slow the progression of insulin resistance or its symptoms. Insulin resistance is the diminished ability of insulin to exert its biological action across a broad range of concentrations producing less than expected biologic effect. Insulin resistant persons have a diminished ability to properly metabolize glucose and respond poorly, if at all, to insulin therapy. Symptoms of insulin resistance include insufficient insulin activation of glucose uptake, oxidation and storage in muscle and inadequate insulin repression of lipolysis in adipose tissue and of glucose production and secretion in cells. Insulin resistance can cause or contribute to polycystic ovarian syndrome, impaired glucose tolerance, gestational diabetes, hypertension, obesity and atherosclerosis. The compositions or formulations derived from this solid state form can be used to reduce triglyceride levels in patients who are insulin resistant.

Decreases in hyperglycemia resulting from treatment with the invention compositions and formulation described herein can be observed as a decrease in the level of blood or serum glucose to a normal fasting range, which for humans at least 2 years of age is about 70 mg/dL to 105 mg/dL or 115 mg/dL, with hyperglycemia being present at fasting glucose levels of about 135 mg/dL or about 140 mg/dL to 200 mg/dL, 300 mg/dL or 350 mg/dL. Glucose levels above about 400 mg/dL are life threatening. Postprandial glucose in blood or serum typically is measured at 2 hours after ingestion of carbohydrates, at least 75 g for humans, followed by a blood draw to measure glucose. Human glucose levels of 140 mg/dL to 200 mg/dL in postprandial blood or serum indicate a hyperglycemia condition and a glucose level above 200 mg/dL identifies human diabetes mellitus. For humans, typically in patients having a normal fasting glucose level of 70-115 mg/dL, an oral glucose tolerance test (OGTT) using blood can be conducted. In the OGTT for humans, if the peak glucose level (typically at 30 min or 1 hour after feeding) and 2 hour post carbohydrate values are above 200 mg/dL on two or more occasions, indicates that the patient has diabetes mellitus.

A surrogate for blood glucose in humans is measurement of glycosylated hemoglobin or Hb A1c, which is used, e.g., to monitor a diabetes treatment. Measurement of Hb A1c allows assessment of blood glucose or sugar levels over 100 to 120 days before the test and it is insensitive to short term variations such as a recent meal or fasting state. Hb A1c levels of 2.2-48% are normal in adults, while levels of 2.5-5.9% indicate good control of diabetes, levels of 6-8% indicate fair diabetes control and levels above 8% Hb A1c indicate poor control of a diabetes condition. Procedures to conduct and interpret these and related protocols have been described, e.g., K. D. Pagana and T. J. Pagana, Mosby's Diagnostic and Laboratory Test Reference, 5th edition, 2001, Mosby Inc., pages 441-448, 451-458, 507-509. Treatments with a formula 1 compound in some embodiments can be monitored by observing decreased Hb A1c, which correlates with improved diabetes treatment or improved glucose control.

Practice of the claimed methods or other methods described herein can result in normalization, e.g., return to levels within normal limits or ranges or near normal limits or ranges of glucose, glucose surrogate or other values such as levels of phase reactive proteins or lipid components such as total cholesterol, e.g., reduced LDL-cholesterol or increased HDL-cholesterol. Normalization of glucose or surrogate values is typically observed as an elevated glucose or surrogate level dropping to within about 1%, about 2%, about 3% or about 5% of a normal glucose level or within about 5% or about 8% of a normal glucose surrogate value. Glucose values for other species have been described and similar measurements or assays can be used in the invention methods for those species. Normalization of other values is typically observed as a return of an abnormally high or low level to within about 2% or about 4% to about 6%, about 10% or about 12% of the upper or lower end of the value's normal range for the subject species.

The invention compositions and formulations described herein can be used to slow the progression or delay the onset of hyperglycemia or to increase insulin sensitivity in insulin resistance where these exist or are reasonably expected to develop. Other effects of these compounds include a decreased glucose intolerance, slowed progression or rate of loss of pancreatic β-islet cell numbers or their capacity to secrete insulin or increased pancreatic β-islet cell numbers or capacity to secrete insulin.

In some embodiments, the methods can be conducted in obese subjects. Obesity or "overweight" for humans as used herein generally refers to (1) an adult human male having a body mass index of about 26 kg/m$^2$, 27 kg/m$^2$, 28 kg/m$^2$, 29 kg/m$^2$, 30 kg/m$^2$, 31 kg/m$^2$, 32 kg/m$^2$ or greater and adult human females having a body mass index of at least about 26 kg/m$^2$, 27 kg/m$^2$, 28 kg/m$^2$, 29 kg/$^2$, 30 kg/m$^2$, 31 kg/m$^2$, 32 kg/m$^2$ or greater or (2) an obese or overweight condition as assessed by a health care provider such as a physician or nurse. The determination of obesity for, e.g., a human, can take body fat content and distribution into account, since some persons with a high body mass index may not technically be obese due to a high amount of muscle tissue instead of fat or adipose tissue or due to a significant mounts of body fat or adipose in body areas other than the abdomen, e.g., hips or pelvis. Obesity and body mass index has been described, e.g., G. A. Colditz, Med. Sci. Sports Exerc., 31(11), Suppl., pp. S663-S667, 1999, F. J. Nieto-Garcia et al., Epidemiology, 1(2):146-152,1990, R. H. Eckel, Circulation, 96:3248-3250, 1999.

In some embodiments, the invention compositions and formulations identified by the invention methods do not significantly activate one or more of a mineralcorticoid receptor, a progesterone receptor, a glucocorticoid receptor, an androgen receptor an estrogen receptor-α, estrogen receptor-β or a biologically active variant of any of these biomolecules in human or mammalian cells in vitro by more than about 10%, about 20% or about 30% when compared to suitable negative control human or mammalian cells, typically as determined in and in vitro assay. Methods to measure these activities have been described, e.g., U.S. Pat. No. 5,298,429. In one exemplary method, an assay for evaluating whether a test compound is a functional ligand for a hormone receptor protein, or a functional engineered or modified form thereof comprising: (a) culturing cells which contain: non-endogenous DNA which expresses the hormone receptor protein, or functional engineered or modified form thereof, and DNA which encodes an operative hormone response element linked to a reporter gene, wherein the culturing is conducted in the presence of at least one test compound whose ability to function as a ligand or modulator for the hormone receptor protein, or functional engineered or modified form thereof, is sought to be determined, and (b) assaying for evidence of transcription of said reporter gene in said cells. This assay will typically be conducted using mammalian cells, e.g., CV-1 or COS cells. The reporter gene can be contained in a reporter plasmid where the non-endogenous DNA expresses the hormone receptor protein or functional modified form thereof is contained in an expression plasmid, wherein said reporter and expression plasmids also contain the origin of replication of SV-40. Also, the reporter gene can be contained in a reporter plasmid, wherein the non-endogenous DNA, which expresses the hormone receptor protein or functional modified form thereof, is contained in an expression plasmid, where the reporter and expression plasmids also contain a selectable marker. Related assays can use stably transfected cells with detectable reporter genes, e.g., as described for estrogen receptor-β (ERβ-UAS-bla GripTite™ cell-based Assay, Catalog Number K1091, Invitrogen Corp.), estrogen receptor-α (ERα-UAS-bla GripTite™ 293 cell-based Assay Catalog Number K1090, Invitrogen Corp.), androgen receptor (AR-UAS-bla GripTite™ 293 MSR cell-based Assay, Catalog Number K1082, Invitrogen Corp.) or progesterone receptor (Progesterone Receptor-UAS-bla HEK293T Assay, Catalog Number K1103, Invitrogen Corp.).

One embodiment comprises a method to treat a condition described herein comprising administering to a subject in need thereof an effective amount of Compound 1. In conducting such methods, the subjects or mammals, e.g., rodents, humans or primates, are optionally monitored for e.g., amelioration, prevention or a reduced severity of a disease, condition or symptom. Such monitoring can optionally include measuring one or more of cytokines (e.g., TNFα, IL-13, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times after treatment with a formula 1 compound such as at about 2-45 days after treatment with a formula 1 compound has ended.

Bone Loss and Repair Conditions.

Claimed embodiments may recite the use of Compound 1 or invention compositions or formulations containing or prepared from a solid state form of F1C and one or more excipients to treat, prevent, delay the onset of or slow the progression of bone loss, bone fracture or osteopenia disorders, e.g., an osteoporosis condition such as primary osteoporosis, postmenopausal or type 1 osteoporosis, involutional or type 2 osteoporosis, idiopathic osteoporosis, a secondary osteoporosis such as a glucocorticoid associated bone loss condition and bone loss associated with a trauma such as a first, second or third degree thermal, chemical or radiation burn. These treatments can improve bone mass, bone density and/or bone strength over time.

Drug Products.

In some embodiments, the invention provides a drug product for treating an inflammation, autoimmune or other condition described herein. The drug product typically comprises (a) a drug (i.e., Compound 1) in a dosage form such as a solid or liquid formulation suitable for, e.g., oral or parenteral administration. Packaging for the drug and/or a package insert or label will have information about the drug's efficacy, mechanism of action, the intended patient population, dosage, dose regimen, route of administration, toxicity of the biological insult or the severity of insult that the drug can be used to treat, if this is known. The drug product can optionally contain a diary or use instructions for the patient to record when or how the drug is used or what symptoms or drug effects the drug user experiences during or after use of the drug. This can be used to aid in phase IV or post marketing analyses of the drug's efficacy or side effects. Other embodiments of drug products are as described in other embodiments described herein.

A drug product as used herein means a product that has been reviewed and approved for marketing or sale by a regulatory agency or entity with authority to review or approve applications for sale or medical use, e.g., the U.S. Food and Drug Administration or the European Medicines Agency or European Medicines Evaluation Agency. Uses of drug products include its marketing or sales and offers to sell or buy it for consideration. These activities will typically adhere to terms of the regulatory approval that may affect or govern marketing, sales, purchases or product handling. The drug in a drug product can be a new drug, a generic drug, a biological, a medical device or a protocol for the use of any of these. The drug product usually results from marketing approval by the U.S. Food and Drug Administration or by the European Medicines Evaluation Agency of a U.S. or non-U.S. new drug application, an abbreviated new drug application, a biological license application or an application to market a medical device. Uses for the drug product include its sale to public or private buyers such as the U.S. Department of Defense, the U.S. Department of Energy, U.S. Department of Health and Human Services or a private drug buyer or distributor entity. Other uses include use of the drug to treat indicated or approved medical conditions and physician approved uses or off label uses. Pre-approval drug products are other aspects of the invention, which may be essentially the same as drug products described herein, but it can be used to prepare a drug or regulatory submission for marketing or for regulatory review before marketing approval.

The intended patient population identified by the drug product can also specify excluded populations, if any that may apply such as pediatric patients or elderly patients. Information about dosage will typically specify daily doses of the drug, while the dose regimen will describe how often and how long the drug is to be administered or taken. The route of administration will identify one or more routes that are suitable for use of the drug, although a given formulation will typically be approved for only one route of administration. Dosages, dose regimens and routes of administration that the package or label may identify are described elsewhere herein.

In one embodiment, the drug product is for treatment, prevention or amelioration of an inflammation condition or another condition described herein and it comprises or includes a formulation that contains a solid state form of Compound or is prepared from the solid state form formulated with 1, 2, 3, 4 or more excipient(s) for oral or parenteral administration, e.g., intramuscular, subcutaneous or subdermal injection, with a package insert or label describing administration of a daily dose of, e.g., about 0.01 mg, 0.05 mg, 0.1 mg, 0.5 mg, 1 mg, 4 mg, 5 mg, 10 mg, 20 mg, 25 mg, 40 mg, 50 mg, 80 mg, 100 mg, 150 mg, 175 mg, 200 mg, 225 mg, 250 mg, 300 mg, 350 mg, 400 mg, 450 mg or 500 mg of a formula 1 compound for 1, 2, 3, 4, 5, 6, 7, 8, 9, 10 or more consecutive days beginning after the disease or condition is diagnosed or otherwise observed. Information that the package insert or label can contain includes information about biological responses to the drug or the treatment regimen. The information can include a description of one or more of (a) one or more side-effects or toxicities associated with use of the drug in humans or mammals such as non-human primates, (b) its effect on the inflammation or other condition, e.g., in a protocol or suitable variation described herein, (c) protocols or instructions for the use of additional therapeutic agents such as dexamethasone or other glucocorticoids with the drug and (d) the time or time period when administration of the drug should begin for best or known therapeutic benefit.

Other invention embodiments include a dietary supplement product or nutraceutical product that comprises or contains (1) androst-5-ene-3β,7β,16α,17β-tetrol, usually the solid state form of androst-5-ene-3β,7β,16α,17β-tetrol described herein, e.g., as described in the claims as originally filed or the synthesis example, (2) suitable packaging and/or labeling for the product, and optionally (3) wherein the solid state androst-5-ene-3β,7β,16α,17β-tetrol is present in a suitable dosage form that contains the compound and one, two or more excipients. The dosage form will typically and preferably be a tablet, capsule, gelcap, soft gel or the like for oral administration. Less preferred but also suitable dosage forms are solid state androst-5-ene-3β,7β,16α,17β-tetrol as a powder or granules and optionally one or more excipients. These dosage forms are typically taken orally alone or as a mixture with other excipients, fluids and/or food. Containers for product containing powder or granules in a suitable container, e.g., screw top bottle, may also include a dispensing scoop or spatula to facilitate dispensing a controlled amount of product from its container and optionally instructions for use of the dispensing device. Typical unit dosages comprising solid state androst-5-ene-3β,7β,16α,17β-tetrol will generally contain about 5 µg to about 10 mg of the solid compound, preferably about 10 µg to about 5 mg. Such unit doses may be taken once or twice per day with or without food or fluids. Typical unit doses are about 0.05 mg, about 0.1 mg about 0.5 mg and about 2 mg. Package or label information will typically conform to applicable disclosure requirements, which will usually include a statement that, e.g., the product is not intended to treat, diagnose, prevent or cure any medical condition or disease. Such dietary supplement products may optionally comprise or contain one or more vitamins such as vitamin C, a vitamin B or vitamin A and/or a mineral nutrient such as a suitable calcium or iron compound.

Dosing Protocols or Methods.

In treating any of the conditions or symptoms disclosed herein, one can continuously (daily) or intermittently administer an invention composition or formulation described herein to a subject suffering from or susceptible to the condition or symptom. In treating a condition such as an inflammation condition or another condition disclosed herein, intermittent dosing could avoid or ameliorate some of the undesired aspects normally associated with discontinuous dosing. Such undesired aspects include failure of the patient or subject to adhere to a daily dosing regimen or reduction of the dosages of other therapeutic agents such as glucocorticoids and/or their associated unwanted side effects or toxicities such as bone loss or resorption.

In some embodiments, daily dosing will continue as long as the disease or symptoms are apparent, typically for chronic conditions. In other embodiments, daily dosing will continue for 1, 2, 3, 4, 5, 6, 7, 8, 9 or 10 consecutive days and then be followed by a period of no dosing until or if dosing is again needed. These embodiments will typically involve treating acute conditions that may or may not recur from time to time. Treatment of chronic conditions will typically involve continuous daily dosing for extended periods of time.

In any of continuous (daily) or intermittent dosing regimen, or in treating any of the diseases, conditions or symptoms described herein, the formula 1 compound(s) can be administered by one or more suitable routes, e.g., oral, buccal, sublingual, topical, intramuscular, subcutaneous, subdermal, intravenous, intradermal or by an aerosol.

The daily dose is usually about 0.001 mg/kg/day to about 200 mg/kg/day. Typical dose ranges are about 0.1 to about 100 mg/kg/day, including about 0.2 mg/kg/day, 0.5 mg/kg/day, about 1 mg/kg/day, about 2 mg/kg/day, about 4 mg/kg/day, about 5 mg/kg/day or about 6 mg/kg/day. One can administer the formula 1 compound(s) orally or by parenteral administration using about 2 to about 50 mg/kg/day or about 2-40 mg/kg/day. Such dosing will typically give a serum level of the formula 1 compound of about 1 ng/mL, about 4 ng/mL or about 8 ng/mL to about 125 ng/mL or about 250 ng/mL, e.g., about 15 ng/mL to about 120 ng/mL or about 20 ng/mL to about 100 ng/mL. Such a serum level can be transient, e.g., lasting about 30 minutes or about 60 minutes to about 2 hours or about 8 hours, which will may occur on days when the compound is administered or at later time for depot formulations. For humans or other mammals an oral or parenteral daily dose will typically be about 0.01 mg, 0.05 mg, 0.1 mg, 0.5 mg, 1 mg, 4 mg, 5 mg, 10 mg, 20 mg, 25 mg, 40 mg, 50 mg, 80 mg, 100 mg, 150 mg, 175 mg, 200 mg, 225 mg, 250 mg, 300 mg, 350 mg, 400 mg, 450 mg or 500 mg of a formula 1 compound, which can be present as a unit dosage, e.g., tablets, capsules, or other forms for oral administration. Such daily doses can often be about 5 mg/day to about 250 mg/day.

Continuous daily dosing is usually used to treat the chronic conditions described herein. Daily doses are usually given as a single dose, but daily doses can be subdivided into 2 or 3 subdoses. Intermittent dosing protocols include administration of an invention composition or formulation described herein every other day or every third day for a suitable time period. Daily dosing can continue for defined periods followed by no dosing for a fixed or variable period of time. In these embodiments, a disease flare such as a multiple sclerosis, optic neuritis, arthritis, asthma, a colitis condition such as ulcerative colitis or Crohn's disease flare can be treated by daily dosing for about 3, 5, 7, 14 or 28 consecutive days, followed by no further treatment until another flare occurs or begins.

Clinical Conditions and Symptoms.

Claimed embodiments may recite Compound 1 in solid state form, invention compositions or formulations comprising or prepared from the solid state form of Compound 1 and methods described herein to treat, ameliorate, prevent or slow the progression of conditions described herein and/or one or more of their symptoms. Such uses include inhibiting bone resorption, decreasing unwanted side effects associate with or caused by a chemotherapy, e.g., antiinflammatory glucocorticoids. Unwanted inflammation conditions include lung inflammation conditions, e.g., lung fibrosis, emphysema, cystic fibrosis, acute or chronic asthma, bronchial asthma, atopic asthma, ARDS or COPD, or autoimmune disorders such as osteoarthritis, rheumatoid arthritis, a pancreatitis such as autoimmune pancreatitis, systemic lupus erythematosis, lupus erythematosus-related tissue inflammation, lupus erythematosus-related arthritis, lupus erythematosus-related skin changes, lupus erythematosus-related hematologic abnormalities, lupus erythematosus-related kidney impairment, lupus erythematosus-related heart or lung disease, and unwanted lupus erythematosus-related neuropsychiatric or neurological changes.

Symptoms of conditions that can be treated include fever, joint pain (arthralgias), arthritis, and serositis (pleurisy or pericarditis). Administration of other agents can also be used in the present treatments. Thus, pain can be treated using nonsteroidal, anti-inflammatory drugs, such as aspirin, salisylates, ibuprofen, naproxen, clinoril, oxaprozin and tolmetin. Cutaneous features of systemic lupus can be treated with antimalarial drugs, such as hydroxychloroquine, chloroquine and quinacrine. Retinoids such as istretinoin and etretinate can also be used to treat skin symptoms in combination with the compounds described herein. Organ damage can be treated with corticosteroids, usually given orally or intravenously. Corticosteroids that can be used include hydrocortisone (cortisol), corticosterone, aldosterone, ACTH, triamcinolone and derivatives such as triamcinolone diacetate, triamcinolone hexacetonide, and triamcinolone acetonide, betamethasone and derivatives such as betamethasone dipropionate, betamethasone benzoate, betamethasone sodium phosphate, betamethasone acetate, and betamethasone valerate, flunisolide, prednisone and its derivatives, fluocinolone and derivatives such as fluocinolone acetonide, diflorasone and derivatives such as diflorasone diacetate, halcinonide, dexamethasone and derivatives such as dexamethasone dipropionate and dexamethasone valerate, desoximetasone (desoxymethasone), diflucortolone and derivatives such as diflucortolone valerate), fluclorolone acetonide, fluocinonide, fluocortolone, fluprednidene, flurandrenolide, clobetasol, clobetasone and derivatives such as clobetasone butyrate, alclometasone, flumethasone, and fluocortolone.

When oral administration of corticosteroids is insufficient, intravenous methyl prednisolone pulse therapy (high dose)

can be used to treat lupus nephritis and other serious non-renal manifestations, such as hemolytic anemia, central nervous system inflammation (cerebritis), low-platelet counts, and severe pleuropericarditis.

The invention compositions and formulations described herein can be used to treat, prevent or slow the progression of osteoporosis or bone fractures. The treatment of subjects can lead to strengthening of bones and/or reduced loss of bone mass or minerals, resulting in increased resistance to fractures. As used herein, "treating" conditions such as those described herein means that the treatment can result in amelioration, prevention or slowed progression of the conditions, and/or amelioration, prevention or slowed progression of one or more symptoms of such conditions.

Formulations and invention compositions for preparing formulations. Claimed invention embodiments may include formulations described here and elsewhere in this disclosure. While it is possible the solid state form of Compound 1 disclosed herein can be administered alone it is usual to present it within a formulation or use it for preparing solid or liquid formulation comprising Compound 1. The formulations, both for veterinary and for human use, comprise or is prepared from a solid state form of Compound 1 together with one or more excipients and optionally one or more additional therapeutic ingredients. Sometimes Compound 1 is present in the invention compositions and compositions composition in less than about 3% by weight or less than about 2% in Compound 1.

Formulations include compositions comprising 1, 2, 3, 4 or more pharmaceutically acceptable excipients or carriers. The invention compositions are used to prepare formulations suitable for human or animal use. Suitable administration routes for formulations include oral, rectal, nasal, topical (including buccal and sublingual), vaginal, rectal and parenteral (including subcutaneous, intramuscular, intravenous, intradermal, intrathecal, intraocular and epidural). In general, aqueous and non-aqueous liquid or cream formulations are delivered by a parenteral, oral or topical route. In other embodiments, such as the invention intermittent dosing methods, Compound 1 may be present as an aqueous or a non-aqueous liquid formulation or a solid formulation suitable for administration by any of the routes disclosed herein, e.g., oral, topical, buccal, sublingual, parenteral, inhaled aerosol or a depot such as a subcutaneous depot or an intraperitoneal or intramuscular depot. It will be appreciated that the preferred route may vary with, for example, the subject's pathological condition or weight or the subject's response to therapy with Compound 1 or other therapy that is used or that is appropriate to the circumstances.

The formulations include those suitable for the foregoing administration routes. The formulations may conveniently be presented in unit dosage form and may be prepared by any of the methods known in the art of pharmacy. Techniques, excipients and formulations generally are found in, e.g., *Remington's Pharmaceutical Sciences*, Mack Publishing Co., Easton, Pa. 1985, 17$^{th}$ edition, Nema et al., *PDA J. Pharm. Sci. Tech.* 1997 51:166-171, G. Cole, et al., editors, *Pharmaceutical Coating Technology*, 1995, Taylor & Francis, ISBN 0 136628915, H. A. Lieberman, et al., editors, *Pharmaceutical Dosage Forms*, 1992 2$^{nd}$ revised edition, volumes 1 and 2, Marcel Dekker, ISBN 0824793870, J. T. Carstensen. *Pharmaceutical Preformulation*, 1998, pages 1-306, Technomic Publishing Co. ISBN 1566766907. Exemplary excipients for formulations include emulsifying wax, propyl gallate, citric acid, lactic acid, polysorbate 80, sodium chloride, isopropyl palmitate, glycerin, white petrolatum and other excipients disclosed herein.

Formulations, or compositions disclosed herein for use to make formulations suitable for administration by the routes disclosed herein optionally comprise an average particle size in the range of about 0.01 to about 500 microns, about 0.1 to about 100 microns or about 0.5 to about 75 microns. Average particle sizes include a range between 0.01 and 500 microns in 0.05 micron or in 0.1 micron or other increments, e.g., an average particle size of about 0.05, 0.1, 0.5, 1, 1.5, 2.0, 2.5, 3.0, 3.5, 4.0, 4.5, 5.0, 5.5, 6, 7, 8, 9, 10, 15, 20, 25, 30, 35, 40, 50, 60, 75, 85, 100, 120, etc. microns). When formula 1 compounds or compositions that comprise a formula 1 compound are used as intermediates to make a formulation, they may comprise one, two, three or more of these average particle sizes, or size ranges. In preparing any of the compositions or formulations that are disclosed herein and that comprise a formula 1 compound (and optionally one or more excipients), one may optionally mill, sieve or otherwise granulate the compound or composition to obtain a desired particle size.

Thus, one such embodiment comprises a method to treat a condition described herein comprising administering to a subject in need thereof an effective amount of Compound 1 or delivering to the subject's tissues an effective amount of a Compound 1. In conducting such methods, the subjects or mammals, e.g., rodents, humans or primates, are optionally monitored for e.g., amelioration, prevention or a reduced severity of a disease, condition or symptom. Such monitoring can optionally include measuring one or more of cytokines (e.g., TNFα, IL-13, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times after treatment with Compound 1 such as at about 2-45 days after treatment with Compound 1 has ended.

As noted above, in some embodiments a treatment with Compound 1 is combined with a corticosteroid or glucocorticoid. Corticosteroids are used in a number of clinical situations to, e.g., decrease the intensity or frequency of flares or episodes of inflammation or autoimmune reactions in conditions such as acute or chronic rheumatoid arthritis, acute or chronic osteoarthritis, a colitis condition such as ulcerative colitis, acute or chronic asthma, bronchial asthma, psoriasis, systemic lupus erythematosus, hepatitis, pulmonary fibrosis, type I diabetes, type II diabetes or cachexia. However, many corticosteroids have significant side effects or toxicities that can limit their use or efficacy. Compound 1 is useful to counteract such side effects or toxicities without negating all of the desired therapeutic capacity of the corticosteroid. This allows the continued use, or a modified dosage of the corticosteroid, e.g., an increased dosage, without an intensification of the side effects or toxicities or a decreased corticosteroid dosage. The side-effects or toxicities that can be treated, prevented, ameliorated or reduced include one or more of bone loss, reduced bone growth, enhanced bone resorption, osteoporosis, immunosuppression, increased susceptibility to infection, mood or personality changes, depression, headache, vertigo, high blood pressure or hypertension, muscle weakness, fatigue, nausea, malaise, peptic ulcers, pancreatitis, thin or fragile skin, growth suppression in children or preadult subjects, thromboembolism, cataracts, and edema. Dosages, routes of administration and dosing protocols for the formula 1 compound would be essentially as described herein. An exemplary dose of Compound 1 of about 0.5 to about 20 mg/kg/day is administered during the period during which a corticosteroid is administered and optionally over a period of about 1 week to about 6 months or more after dosing with the corticosteroid has ended. The corticosteroids are administered essentially using known dosages, routes of administration and dosing protocols, see, e.g., Physicians Desk Reference 54th edition, 2000, pages 323-2781, ISBN 1-56363-330-2, Medical Economics Co., Inc., Montvale, N.J. However, the dosage of the corticosteroid may optionally be adjusted, e.g., increased about 10% to about 300% above the normal dosage, without a corresponding increase in all of the side effects or toxicities associated with the corticosteroid. Such increases would be made incrementally over a sufficient time period and as appropriate for the subject's clinical condition, e.g., daily corticosteroid dose increases of about 10% to about 20% to a maximum of about 300% over about 2 weeks to about 1 year.

The treatments can also be used to reduce bone loss due to a therapy, e.g., a glucocorticoid therapy in a lupus condition or in patients having an inflammatory bowel disease, Crohn's disease, acute or chronic colitis or a renal disorder such as acute or chronic renal failure or autoimmune renal injury.

Numbered Embodiments

The following embodiments exemplify one or more aspects of the invention are not meant to be limiting in any way.

1. A product wherein the product is a solid state form of androst-5-ene-3β,7β,16α,17β-tetrol obtained by the process comprising (1) obtaining purified androst-5-ene-3β,7β,16α,17β-tetrol (2) recovering androst-5-ene-3β,7β,16α,17β-tetrol from aqueous acetonitrile.

2. The product of embodiment 1 characterized by: (a) an X-ray powder pattern with 2-theta values of about 15.9, 17.3 and 19.2 and optionally one or more 2-theta values of about 7.4, 14.8, 20.4, 24.4, 27.4 and 29.4 and (b) with differential thermal analysis spectrum with a heating rate of 10° C./min having an endothermic transition centered at about 204° C. (onset at about 194° C.) optionally with an endotherm transition centered at about 98° C. or 224° C.

3. The product of embodiment 1 characterized by (a) an X-ray powder pattern with 2-theta values of about 15.9, 17.3 and 19.2 and optionally one or more 2-theta values of about 7.4, 14.8 20.4, 24.4, 27.4 and 29.4 and (b) a solid state infrared Raman spectrum with peaks at about 1670 cm$^{-1}$, 1462 cm$^{-1}$ and 1439 cm$^{-1}$.

4. The product of embodiment 1 characterized by the X-ray powder pattern data, the differential thermal analysis data and the solid state infrared Raman data of embodiments 2 and 3.

5. The product of embodiment 1 having an a solid infrared Raman spectrum substantially identical to FIG. 1.

6. The product of embodiment 1 having an X-ray powder pattern substantially identical to FIG. 2.

7. The product of embodiment 1 having the X-ray powder pattern substantially identical to FIG. 2 and the solid infrared Raman spectrum substantially identical to FIG. 1.

8. A composition comprising one or more excipients and a solid state form of androst-5-ene-3β,7β,16α,17β-tetrol obtained by the process comprising (1) obtaining purified androst-5-ene-3β,7β,16α,17β-tetrol, and (2) recovering androst-5-ene-3β,7β,16α,17β-tetrol from aqueous acetonitrile.

9. A method of preparing a liquid formulation comprising admixing a solid state form of androst-5-ene-3β,7β,16α,17β-tetrol, obtained by the process comprising (1) obtaining purified androst-5-ene-3β,7β,16α,17β-tetrol, and (2) recovering androst-5-ene-3β,7β,16α,17β-tetrol from aqueous acetonitrile, with a liquid excipient.

10. A method of treating an inflammation condition, or disease or another condition or disease described herein, comprising administering an effective amount of a solid formulation to a subject in need thereof wherein the formulation comprises a solid state form of androst-5-ene-3β,7β,16α,17β-tetrol obtained by the steps (1) obtaining purified androst-5-ene-3β,7β,16α,17β-tetrol, and (2) recovering androst-5-ene-3β,7β,16α,17β-tetrol from aquesous acetonitrile.

11. The method of embodiment 10 wherein the inflammation condition or disease is a chronic, non-production inflammation condition or disease.

12. The method of embodiment 10 wherein the condition or disease is an autoimmune condition or disease.

13. The method of embodiment 11 wherein the condition or disease is a metabolic condition or disease.

14. The method of embodiment 12 wherein the autoimmune disease is Type 1 diabetes.

15. The method of embodiment 14 wherein the autoimmune disease is a lupus condition such as systemic lupus erythematosus or discoid lupus, arthritis conditions such as rheumatoid arthritis or osteoarthritis.

16. The method of embodiment 11 wherein the condition or disease is an inflammatory bowel disease such as ulcerative colitis or Crohn's disease (regional enteritis).

17. The method of claim 11 wherein the condition or disease is a lung inflammation condition such as cystic fibrosis, chronic obstructive pulmonary disease (COPD), acute asthma, chronic asthma, emphysema, acute bronchitis, allergic bronchitis, chronic bronchitis and fibrosing alveolitis (lung fibrosis) conditions, e.g., subepithelial fibrosis in patients having chronic bronchitis, asthma and/or COPD.

18. The method of claim 11 wherein the condition or disease is a neurodegenerative condition such as Parkinson's disease or Alzheimer's disease.

19. The method of claim 11 wherein the condition or disease is a hyperproliferation condition.

20. The method of claim 11 wherein the condition or disease is a liver cirrhosis condition, nonalcoholic steatohepatitis (NASH) or fatty liver conditions.

21. The method of embodiment 13 wherein the metabolic condition or disease is type 2 diabetes, obesity, insulin resistance, hyperglycemia, impaired glucose utilization or tolerance, impaired or reduced insulin synthesis, 22. A method to prepare androst-5-ene-3β,7β,16α,17β-tetrol comprising saponifying 3β,16α-diacetoxyandrost-5-ene-7β,17β-diol, purifying the mixture and recovering androst-5-ene-3β,7β,16α,17β-tetrol.

23. The method of embodiment 22 wherein the 3β,16α-diacetoxyandrost-5-ene-7β,17β-diol is saponified in methanol with sodium hydroxide.

24. The method of embodiment 23 wherein androst-5-ene-3β,7β,16α,17β-tetrol is recovered from aqueous acetonitrile.

25. A drug product or pre-approval drug product comprising a drug in a dosage form and packaging for the drug together with a package insert or label that includes information about the drug's efficacy, mechanism of action or clinical use 26. A drug product or pre-approval drug product comprising a drug (i.e., Compound 1) in a dosage form and packaging for the drug together with a package insert or label that includes information about the drug's efficacy, mechanism of action or clinical use, wherein the efficacy, mechanism of action or clinical use information was obtained at least in part from a characterization method that comprises (a) contacting a cell or cells in vitro for a sufficient time with a sufficient amount of an activator of NF-κB activity wherein the cell(s)

can respond to the activator of NF-κB by detectably increasing the level or activity of NF-kB in the cell(s); (b) contacting the cell(s) in vitro for a sufficient time with a sufficient amount of the drug, wherein the drug detectably inhibits the activation of NF-κB activity compared to suitable control; and (c) optionally comparing the drug's capacity to inhibit activation of NF-kB with a reference compound, wherein the reference compound has the capacity to detectably inhibit activation of NF-κB in the characterization method by about 25% to about 75%, wherein the drug inhibits activation of NF-kB by about 25% to about 75% in the characterization method and optionally wherein the reference compound or the drug does not detectably or significantly bind directly to a glucocorticoid receptor or optionally wherein the reference compound or the drug does not detectably or significantly agonize a glucocorticoid receptor, optionally the drug does not agonize a glucocorticoid receptor by more than about 20% compared to a suitable agonist control.

27. The drug product of embodiment 25 or 26 wherein the dosage form comprises an oral, parenteral, topical or inhalation formulation.

28. The drug product of embodiment 25 or 26 wherein the reference compound or the drug inhibits activation of NF-kB by about 35% to about 70% or by about 40% to about 65% in the characterization method.

29. The drug product of embodiment 25, 26 or 27 wherein the NF-κB in the cells is activated by one, two, three or more of TNF-α, TNF-β, TGF-β, IL-1, epidermal growth factor, bacterial LPS, bacterial peptidoglycan, yeast zymosan, bacterial lipoprotein, a bacterial or viral antigen or gene product, ultraviolet irradiation, heat or a temperature increase, a lymphokine or an oxidant free radical, or $H_2O_2$.

30. The drug product of embodiment 25, 26, 27 or 28 wherein the reference compound or the drug binds directly to a glucocorticoid receptor with a $k_d$ of >10 μM in a suitable binding assay or wherein the reference compound or the drug does not detectably agonize a glucocorticoid receptor at a concentration of equal to or greater than about 10 μM in an assay suitable to detect activation or an increase of glucocorticoid receptor-mediated gene expression.

31. The drug product of embodiment 25, 26, 27 or 28 wherein the cell(s) in vitro are mammalian, rodent or human cell(s) optionally selected from the group consisting of human THP-1 cells, rat RAW cells, macrophages, monocytes, T-lymphocytes, B-lymphocytes, dendritic cells, glial cells, Kupfer cells, hepatocytes, neutrophils, white blood cells and cells from whole blood.

32. The drug product of embodiment 25 or 26 wherein the information about the drug's efficacy, mechanism of action or clinical use is included in a submission to a regulatory agency or a review entity with authority to review or approve the commercial use or marketing of the drug product.

33. A method to treat an inflammation condition or autoimmune disease in a mammal, comprising administering to the subject, or delivering to the subject's tissues, an effective amount of an invention composition or formulation comprised of or prepared from the solid state form of Compound 1 disclosed herein.

34. A solid state form of Compound 1 wherein Compound 1 is (a) a powder or granule that is at least 80% pure, at least 95% pure or at least 98% pure or (b) a solution or suspension that is at least 80% pure, at least 95% pure or at least 98% pure.

35. The solid state of embodiment 28 wherein Compound 1 is about 80%, about 85%, about 90%, about 95%, about 97% or about 98% to about 99.5% or about 99.9% pure, optionally wherein Compound 1 is in the form of a powder or granules, optionally wherein the powder has an average particle size of about 50 nm or about 100 nm to about 5 μm, about 10 μm or about 25 μm as measured in a suitable assay such as light scattering.

36. A method of treatment or prophylaxis of an autoimmune disease or unwanted inflammation condition, which optionally is an arthritis condition such as an osteoarthritis (primary or secondary osteoarthritis), rheumatoid arthritis, an arthritis associated with spondylitis such as ankylosing spondylitis, multiple sclerosis, Alzheimer's disease, tenosynovitis, a lupus condition such as systemic lupus erythematosis or discoid lupus erythematosis, tendinitis, bursitis, a lung inflammation condition such as asthma, emphysema, chronic obstructive pulmonary disease, lung fibrosis, cystic fibrosis, acute or adult respiratory distress syndrome, chronic bronchitis, acute bronchitis, bronchiolitis, bronchiolitis fibrosa obliterans, bronchiolitis obliterans with organizing pneumonia, using Compound 1.

37. The method of embodiment 36 comprising administering to the human or the rodent a treatment effective amount of Compound 1. Such treatments include treatment with about 0.1 mg/day, about 1 mg/day or about 5 mg/day to about 40 mg/day or about 80 mg/day of Compound 1.

38. The method of embodiment 37 wherein the autoimmune or related disorder is ulcerative colitis, inflammatory bowel disease, Crohn's disease, psoriasis, actinic keratosis, arthritis, multiple sclerosis, optic neuritis or a dermatitis condition, optionally contact dermatitis, atopic dermatitis or exfoliative dermatitis.

Variations and modifications of these embodiments and other portions of this disclosure will be apparent to the skilled artisan after a reading thereof. Such variations and modifications are within the scope of this invention. The claims in this application or in applications that claim priority from this application will more particularly describe or define the invention. All citations or references cited herein are incorporated herein by reference in their entirety at this location or in additional paragraphs that follow this paragraph. Other descriptions are found in application Ser. No. 11/941,936, filed Nov. 17, 2007, U.S. provisional application Ser. No. 60/866,395, filed Nov. 17, 2006, U.S. provisional application Ser. No. 60/866,700, filed Nov. 21, 2006, U.S. provisional application Ser. No. 60/868,042, filed Nov. 30, 2006, U.S. provisional application Ser. No. 60/885,003, filed Jan. 15, 2007, U.S. provisional application Ser. No. 60/888,058, filed Feb. 2, 2007, all of which are incorporated herein by reference.

EXAMPLES

The following examples further illustrate the invention and they are not intended to limit it in any way.

Example 1

Treatment of lung inflammation. Compound 1 is used to treat inflammation in mice essentially as described (D. Auci et al., Ann. New York Acad. Sci. 1051:730-742 2005). Five to 8 week old CD1 male mice (Charles River, Calco, Italy) are used for the study. The animals are housed in a controlled environment and provided with standard rodent chow and water. Animal care is in compliance with applicable regulations on protection of animals. Mice are allocated into one of the following groups: (1) mice to be treated with 2% carrageenan-λ in saline (carrageenan-λ treated control group), (2) mice to be treated with 0.1 mg, 0.01 mg or 0.001 mg by Compound 1 by subcutaneous (s.c.) injection 24 h and 1 h before carrageenan-λ administration, (3) mice treated with vehicle (0.1% carboxymethylcellulose, 0.9% saline, 2% tween 80, 0.05% phenol) s.c. 24 h and 1 h before carrageenan-λ administration; (4) mice to be treated with rabbit anti-mouse polyclonal anti-TNF-α antibody (200 µg) to be given as an intraperitoneal bolus 24 h and 1 h before carrageenan-λ administration (positive control group); and (7) sham-operated mice that will not be treated with carrageenan-λ. Each group consists of 10 mice. All treatments are given in a final volume of 100 µL. Lung (pleural cavity) inflammation is induced as follows. The mice are anaesthetised with isoflurane and a skin incision is made at the level of the left sixth intercostal space. The underlying muscle is dissected and either 0.1 mL saline (control) or 0.1 mL saline containing 2% λ-carrageenan was injected into the pleural cavity. The carrageenan-λ is a potent inducer of inflammation, which is manifested in this protocol by accumulation of fluid and neutrophils in the pleural cavity. The incision is closed with a suture and the animals are allowed to recover.

At 4 h after the injection of carrageenan-λ, the animals are euthanized by exposure to $CO_2$. The chest is carefully opened and the pleural cavity is to be rinsed with 1 mL of saline solution containing heparin (5 U/mL) and indomethacin (10 µg/mL). The exudate and washing solution are removed by aspiration, and the total volume is measured. Any exudate contaminated with blood is discarded. The amount of exudate is calculated by subtracting the injected 1 mL volume from the total pleural cavity volume that is recovered. The neutrophils in the exudate are suspended in phosphate-buffer saline and are to be counted with an optical microscope in a Burker's chamber after Trypan Blue staining. The results are analysed by one-way ANOVA followed by a Bonferroni post-hoc test for multiple comparisons. A p-value less than 0.05 is considered significant. For statistical analysis each group is compared to the control group of mice that will be challenged with carrageenan-λ and will receive no other treatment.

All of the mice that are challenged with carrageenan-λ and are left untreated will develop an acute pleurisy, producing turbid exudate and increased pleural numbers of neutrophils. The increase in volume exudates and numbers of leukocytes in the pleura of the mice treated with the vehicle is similar to that observed in the control mice that are challenged with carrageenan-λ and received no treatment.

Example 2

A known side effect of antiinflammatory glucocorticoid compounds such as dexamethasone is IL-13 rebound that makes an asthma patient more prone to have subsequent acute flare, so an antiinflammatory agent that does not do this would be advantageous. Lack of an IL-13 rebound is unexpected.

The capacity of Compound 1 to limit eosinophil burden and to reduce key inflammatory mediators (IL-5, IL-13, cysteinyl leukotrienes) is observed in the ovalbumin (OVA) sensitized mouse model of asthma. BALB/c mice are sensitized by intraperitoneal injection with OVA (in alum adjuvant) on days 1, and 12. Airways are challenged with OVA on days 28 and 30 by delivery of OVA to the lung, or with saline. On day 31, typically six mice are treated with saline and 6 mice challenged with OVA are sacrificed and lung tissue is analyzed. The remaining animals are divided into 6 groups (6 mice per group). Groups of the mice are treated once daily by subcutaneous injection as follows. Group 1: vehicle control (0.1% carboxymethyl cellulose, 0.9% saline, 2% tween 80, 0.05% phenol). Group 2: dexamethazone (5 mg/kg). Group 3: Compound 1 (1 mg/mouse). Three animals in groups 1-3 were sacrificed on day 35 at 1 hr after final treatment and the remaining 3 animals in groups 1-3 are sacrificed on day 38.

In another protocol, a population of mast cells are cultivated from murine bone marrow as follows. Briefly, bone marrows from Balb/C mice are flushed from the femur using PBS and a 27 g needle. The cells are cultured in a mixture of ⅔ RPMI-1640 with 19% FBS and cells that secrete IL-3. The bone marrow cells are allowed to differentiate for 18-25 days in the IL-3-containing mixture before being used for experiments. Bone marrow cells cultured in this manner have a phenotype similar to mucosal mast cells and are referred to as bone marrow-derived mast cells (BMMC).

The homogeneity of the in vitro propagated mast is checked by conventional flow cytometry techniques and staining for cell-type specific markers. Between days 14 and 21 of propagation, mature mast cells are harvested and prepared for the test cultures. The objective is to assess of the effect of dehydroepiandrosterone on mast cell stimulus-coupled degranulation. Prepared mast cells are dispensed into test culture wells at a density of $1 \times 10^7$ cells/mL. In control cultures, mast cells are induced to degranulate after cross linking of IgE receptors with IgE antigen-antibody complexes. In parallel groups of cultures mast cells were preincubated dehydroepiandrosterone at various doses followed by activation using anti-IgE antibody. There is no detectable degranulation of mast cells as measured by release of β-glucuronidase from cytosolic storage granules of the cells in the absence of the stimulus. Introduction of anti-Ig-E receptor antibody to the cultures causes a significant release of β-glucuronidase. When mast cells were exposed to dehydroepiandrosterone alone, typically there was no measurable degranulation. However, mast cells pre-exposed to doses of 100 µM dehydroepiandrosterone for 5 to 10 minutes before activation with anti-IgE antigen-antibody complexes, exhibit approximately 70% inhibition of degranulation. Lower levels of dehydroepiandrosterone showed proportionately less capacity to inhibit degranulation. In similar protocols, androst-5-ene-3β,7β,16α,17β-tetrol (i.e., Compound 1) was 10-1000 fold more potent than dehydroepiandrosterone.

Example 3

Anti-inflammation activity in human cells in vitro. The capacity of Compound 1 and 16α-bromoepiandrosterone to reduce inflammation in human cells in vitro is demonstrated using human whole blood that are exposed to LPS. Reduced production of γ-interferon by the cells are observed in the presence of 16α-bromoepiandrosterone (100 ng/mL) and Compound 1 compared to cells exposed to LPS alone (positive control) or vehicle (dimethylsulfoxide) without compound (vehicle control). The amount of γ-interferon is measured in the growth medium when the cells had been incubated in the presence of LPS for 24 hours.

Example 4

Treatment of autoimmune neurodegeneration. The capacity of Compound 1 and other compounds to treat multiple sclerosis was evaluated in experimental autoimmune encephalomyelitis (EAE). The protocol for conducting the EAE animal model was described in (D. Auci et. al., *Ann. NY. Acad. Sci. USA*, 1051:730-42, 2005). In this protocol, Compound 1 was administered to female SJL/J mice by oral gavage at the onset of disease symptoms. An antigen was used to initiate the EAE condition in the mice. The antigen that was used for the active immunization is mouse proteolipid protein (PLP) residues 139-151. Immunization with this peptide antigen initiates an autoimmune Th1 mediated demyelinating disease of the central nervous system. The antigen was prepared by solid phase synthesis and purified by high-performance liquid chromatography. The EAE condition was initiated in the female SJL/J mice by immunization with 150 μg of the PLP 139-151 peptide in complete Freund's adjuvant containing 200 μg of *Mycobacterium tuberculosis*. The immunization protocol was subcutaneous injection over four sites on the hind flank on day 0. Mice in the vehicle control group began to show observable symptoms of EAE at about 10-11 days after immunization with the PLP antigen, which is typical for the EAE disease model. The animals were dosed daily with Compound 1 by oral gavage beginning at day 1, which was 1 day after immunization.

Female SJL mice (6-8 week old, average body weight of 25 g) obtained from Charles-River were kept under standard laboratory conditions (non specific pathogen germ free) with ad libitum food and water and were allowed to adapt one week to their environment before commencing the study. Animals were randomized into six groups of seven animals and included (1) mice treated with vehicle, (2) mice treated with SU5416 (Z-3-[(2,4-dimethylpyrrol-5-yl)methylidenyl]-2-indolinone), (3) mice treated with androst-5-ene-3β,7β,16α,17β-tetrol, (5) mice treated with androst-5-ene-3β,7β,16α,17β-tetrol. EAE was induced with 200 μL of a 1:1 emulsion of 75 μg proteolipid protein (PLP) and 6 mg/mL *Mycobacterium tuberculosis* H37RA in complete Freund's adjuvant (CFA). The 200 μL injection was divided among four sites that drained into the auxiliary and inguinal lymphnodes. Pertussis toxin was used as a co-adjuvant and was administered i.p. at 200 ng/mouse on day zero and day two post immunization. Groups were treated with 0.1 mg of compound in 100 μL vehicle, or with vehicle alone, q.d. po (oral gavage) starting at clinical onset of disease and continuing through to day 30 post immunization. Clinical onset is defined as the time when clinical symptoms of the disease attain a grading between 2-3 in 25% of the mice. Clinical grading was carried out by an observer unaware of the treatment: 0=no illness, 1=flaccid tail, 2=moderate paraparesis, 3=severe paraparesis, 4=moribund state, 5=death. Statistical analysis for significant differences on clinical scores were performed by ANOVA for unpaired data and to the non parametric Mann-Whitney test. A P value <0.05 was considered to be statistically significant. For statistical analysis, the mice that succumbed to EAE were assigned 5 only for the day of death and then were deleted from the experimental group.

As expected, classical signs of EAE developed in 8/8 (100%) of the vehicle-treated mice within day $19^{th}$ post immunization. The mean day of onset was 15.5±3.9 (SD). In this group of animals the duration of the disease was 12.3±4.3 days. The mean cumulative score from day 1 to 30 was 24.8±7.8 and that from day 31 to day 54 (post treatment) was 22.7±15.8. Mice treated with androst-5-ene-3β,7β,16α,17β-tetrol (i.e., Compound 1) exhibited a significantly improved course of EAE as compared to the vehicle-treated mice entailing significantly reduction of both one or more the mean cumulative score and duration.

These results show that Compound 1 exerted powerful anti-inflammatory properties in the PLP-induced model of EAE in SJL mice. Of particular relevance for the translation of these findings to the clinical setting are the observations that Compound 1 was active in this EAE model even when given in a protocol starting on day $12^{th}$ post immunization when 24% of the mice had already developed clinical signs of EAE. Of particular note is the finding that SU5416 was ineffective in this setting. It has been previously reported that SU5416 is effective in EAE (L. Bouerat et al., *J. Med. Chem.* 48: 5412-5414, 2005). However, to obtain this result, the SU5416 compound was administered at the same time the animals were immunized. By contrast, in this protocol compounds such as Compound 1 were not administered to the animals until after disease symptoms were apparent, which shows that such compounds can be used to effectively treat existing disease and to prevent or delay disease onset.

Example 5

Inhibition of NF-κB in vitro. A number of compounds including Compound 1 were used to inhibit activation of NF-κB by TNF-α or LPS in human cells in vitro. Activation of NF-κB increases expression of a number of genes that mediate inflammation. This protocol used human THP-1 cells, which are human mononuclear blood cells with a monocyte phenotype. The cell line, referred to as NF-κB-bla THP-1, contained a β-lactamase reporter gene under the control of the NF-kB response element (Invitrogen, CellSensor™, product No. K1176). In this cell line, the β-lactamase reporter gene is stably integrated in the THP-1 cells. This cell line was used to detect agonists or antagonists of the NF-κB signaling pathway. These NF-κB-bla THP-1 cells respond to the presence of tumor necrosis factor alpha (TNFα) or bacterial lipopolysaccharide (LPS) by increased expression of the β-lactamase reporter gene. The level of β-lactamase enzyme activity was measured by fluorescence resonance energy transfer ratiometric detection. TNFα and LPS are both potent inflammation-inducing agents that activate NF-κB in THP1 cells. In this assay, compounds that decrease NF-κB activity, and thus β-lactamase, in the presence of TNFα or LPS are exerting an anti-inflammation activity.

The NF-κB-bla THP-1 cells were maintained by passaging or feeding as needed. The cells, which grow in suspension, were maintained at a density between $2 \times 10^5$ cells per mL and $2 \times 10^6$ cells/mL. The cells were plated at 20,000 cells/well in a 384-well Black-wall, clear bottom assay plates (Costar#3712-TC low fluorescence background plates) approximately 24 hours before adding either TNFα at 10 ng/mL or LPS at 0.2 ng/mL to activate NF-κB. In positive control assays for activation of NF-κB, the $EC_{50}$ concentration for TNFα was 0.20 ng/mL after a 1 hour β-lactamase substrate incubation. The $EC_{50}$ dose for LPS was 0.15 ng/mL. The $EC_{50}$ concentration for TNF-α or LPS in this assay refers to 50% of the concentration of TNF-α or LPS that causes a maximum activation of NF-κB. The synthetic glucocorticoid dexamethasone (a potent anti-inflammatory drug) decreased the effect of TNFα by with an $EC_{50}$ of 0.47 nM (average of 5 assays) in this assay. Similar biological activity for dexamethasone has been reported in other in vitro cell assays, with complete inhibition of NF-kB activation observed at an $IC_{50}$ of about 1 nM (M. K. A. Bauer et al., *Eur. J. Biochem.* 243:726-731, 1977).

The capacity of compounds such as Compound 1 to decrease the activity of NF-κB at low levels indicates that they can be used to treat inflammation, particularly in conditions where excess levels or nuclear transcription activity mediated by NF-kB plays a significant role in the pathology of the disease or condition.

In the assay described above, maximum inhibition of NF-κB by dexamethasone, 16α-bromoepiandrosterone and 16β-bromoepiandrosterone was 100%. By contrast, maximum inhibition of NF-κB by 3β,7β,16α,17β-tetrahydroxyandrost-5-ene was less than about 80%, with increasing the amounts of the compounds above its $IC_{50}$ levels not providing significant additional inhibitory activity against NK-κB activation.

Methods to modulate NF-κB that have been described and that can be incorporated into or used in the practice of the present invention include those described in the following publications. U.S. Pat. Nos. 5,989,835, 6,410,516, 6,545,027, 6,831,065 and 6,998,383, which are incorporated by reference into the present disclosure. Other aspects of NF-κB activity have been described and can also be incorporated into the invention methods, e.g., A. S. Baldwin, *Annual Rev. Immunol.* 14:649-683 1996; M. Muller et al., *Mol. Cell. Biol.* 22((4)1060-1072, 2002; P. A. Baeuerle, *Cell* 95:729-731 1998.

Example 6

The capacity of Compound 1 to treat LPS induced inflammation is examined by a protocol similar to the protocol described above. Five groups of three ICR mice weighing about 30 g are each treated by intraperitoneal injection with 120 μL vehicle (30% sulfobutylether-cyclodextrin in water) and androst-5-ene-3β,7β,16α,17β-tetrol (i.e. Compound 1) in vehicle. The sulfobutylether-cyclodextrin is obtained commercially (CAPTISOL™). There are two vehicle control groups, one group that receives vehicle alone and the other that receives vehicle plus LPS. The vehicle or drug is administered 24 hours before and at 1 hour after LPS (about an $LD_{50/24}$ dose, i.e., 50% lethal at 24 hours after LPS administration) is administered to the mice by intraperitoneal injection. Drug is administered at about 40 mg/kg (1.2 mg drug/animal for each administration of the drugs). Spleens are harvested from the animals at 1.5 hours after injection of LPS and spleen cells were lysed and assayed for activated NF-κB by isolating nuclei from spleen cells and measuring NF-κB from the lysed nuclei. The level of activated NF-κB in spleen cells from the animals that are treated with vehicle and no LPS, are essentially the same as the activated NF-κB in spleen cells from drug treated animals. These results indicate a potent anti-inflammation effect in the animals to be shown by a decrease in activated NF-κB in drug treated animals compared to control animals.

Example 7

Kinetic analysis of NF-kB inhibition in vivo. The kinetics of NF-kB inhibition after injection of bacterial LPS in mice is examined to further probe the mechanism of action of Compound 1 and other compounds that will only partially inhibit activation of NF-κB induced by LPS or TNFα in immune cells (macrophages or monocytes) in vitro as described (vide supra). In this study, mice will be treated by intraperitoneal injection of a solution (not a suspension) of compound in the vehicle as previously describe (vide supra). The drug is injected 24 hours before intraperitoneal injection of bacterial LPS (about an $LD_{50/24}$). The study used two groups of 12 animals, vehicle control or drug administered 24 hours before LPS challenge. Spleens are harvested from 3 animals from both groups just before LPS challenge and at 1.5, 2.0 and 2.5 hours after administration of LPS. Spleen cells are harvested and the level of activated NF-κB is measured by assay of NF-κB in nuclei essentially as described in example 8. Maximum NF-κB activation after LPS administration occurs at 1.5 hours in the vehicle controls, which is 4-fold increased over the pre-LPS level of activated NF-κB. The profound inhibition of NF-κB at the 1.5 hour time point and relatively normal levels of NF-κB activity at the other time points indicates that Compound 1 exerts a transient but potent inhibition of LPS induced trauma at a critical period after LPS exposure. Similar assays in other studies showed that the level of activated NF-κB at 30 minutes and 60 minutes after injection of LPS in vehicle control mice was similar to the pre-LPS time point in this study. This result indicates that in this model, the effect of LPS on the activation of NF-κB in spleen cells was maximal at about 1.5 hours post LPS challenge. This time point reveals a convenient time or window at which the activity of Compound 1 can be assessed in vivo, i.e., at about 75 minutes to about 105 minutes after LPS challenge. A component of the beneficial biological activity of such drug candidates can include moderation or reduction of inflammation that is at least transient, e.g., lasting for about 15 minutes or 30 minutes 45 minutes or more. The window can vary, depending on the route of administration of the biological insult, e.g., LPS or TNFα, administered by intraperitoneal injection versus LPS or TNFα administered by subcutaneous or intramuscular injection.

Analysis of LPS induced TNFα expression in mice showed that TNFα levels peaked at 1.5 hours after LPS challenge (500 μg of LPS administered by intraperitoneal injection) with highest levels of TNFα observed at 1-2 hours after LPS challenge. TNFα levels at 30 minutes after LPS and at 2.5 hours were lower.

Example 8

The capacity of Compound 1 to affect the course of arthritis in a passive collagen induced arthritis model of arthritis is examined essentially as previously described (E. Simelyte et al., *Arthritis & Rheumatism,* 52(6):1876-1884, 2005; Z. Han et al., *Arthritis & Rheumatism* 46(3):818-823, 2002; H. Miyahara et al., *Clin. Inmunol. Immunopathol.,* 69(1):69-76, 1993). In this protocol, passive collagen-induced arthritis is induced in DBA/1 mice by administering anti-type 11 collagen antibodies, which induces an immune response against joint tissue in the animals. Efficacy in this model of arthritis shows efficacy primarily against inflammation, which is assessed in isolation from cellular effects that operate in arthritis. The severity of arthritis is assessed using a semi-quantitative clinical scoring system. Groups of 8 animals per group were treated with Compound 1 for 14 days or vehicle for 14 days by oral gavage. The vehicle is 30% cyclodextrin-sulfobutylether in water and the drug solution is vehicle with drug.

The animals are examined by measuring ankle thickness and arthritis score (4-point/paw) with a higher score indicating a more severe arthritis. The experiment is terminated after about 14 days, and histology and gene expression measurements is performed. For histology, the left hind paw is harvested, fixed in 10% formalin for 24 h, decalcified, and embedded in paraffin. Tissue sections are stained with hematoxylin and eosin for safranin O-fast green to determine proteoglycan content. A semi-quantitative scoring system is used to access synovial inflammation, extraarticular inflammation, erosion and proteogylcan loss.

Treatment with Compound 1 begins following administration of the antibodies. The protocol allows observation of the effects of treatment on the progression of arthritis. The results show that collagen induced arthritis in group 1 is reduced in group 1 animals compared to group 4 animals and at days 7-14. Differences in clinical score at days 7-14 are apparent in the treated animals, which show a reduced level of inflammation is present in the treated animals compared to the vehicle control animal group. The capacity of Compound 1 to reduce the severity of arthritis contrasts with suppressors of cell mediated immunity such as methotrexate or anti-TNFα agents, which have little efficacy in this arthritis model.

Example 9

The capacity of Compound 1 and other compounds to affect LPS-induced lung injury in the mouse is investigated using the LPS-induced lung injury models, which previously has been used to evaluate treatments for acute lung injury (ALI), acute adult respiratory distress syndrome (ARDS) and endotoxin shock or sepsis (Metz et al., C., *Chest* 100(4): 1110-9,1991; Windsor, A. C. et al., *Ann. J. Med. Sci.* 306(2): 111-6,1993; Brigham K. L. et al., *Am. Rev. Respir. Dis.* 133 (5): 913-27,1986).

The protocol conducted was essentially as described in Su, X. et al., *Intensive Care Med.* 30:133-140, 2004. Female mice 6-8 week old C57/BL6 mice (average body weight of 25 g) obtained from Jackson Laboratory (Bar Harbor, Me.) were randomized into groups of seven animals and were maintained under standard housing and food. The groups included (1) mice treated with saline and LPS, (2) mice treated with vehicle and LPS (3) mice treated with 125 μg dexamethasone, (4) mice treated with 40 mg/Kg androst-5-ene-3β,7β,16α,17β-tetrol and LPS.

On day −1 mice were pre-treated with compound or vehicle. On day 0 mice were treated with a second dose of compound or vehicle. On day 0+60 minutes, mice were challenged with 100 μg of *E. Coli* LPS (Sigma) under direct visualization of the trachea under light anesthesia. On day 2 (i.e. 48 hour time point after LPS challenge) mice were sacrificed mice and BAL obtained (where cell counts and TNFα/IL6 levels were measured). The lungs were taken, minced and used for myeloperoxidase (MPO) studies. LPS-induced acute lung inflammation was preformed by instilling 50 mg LPS (*E. Coli* 0111:B4, Sigma-Aldrich) in 100 mL PBS into the tracheas of lightly anesthetized (isoflurane) under direct visualization. At 48 h time point, the mice were sacrificed. After this, a tracheotomy is established after exposing the trachea in the lower neck. A blunt ended 20 gauge needle is inserted into the exposed trachea, which is then tied off and used to obtain the bronchioalveolar lavage (BAL). To minimize airway bleeding and trauma, BAL is performed using 0.5 mL of sterile PBS X 3. A total of 1300 mL are typically recovered from this process. Cell differential leukocyte counts are determined in BAL fluid (BALF) using a hemacytometer. Differentials are performed on 80-100 cells. After obtaining the BAL, the chest cavity is opened and the heart/lungs are perfused with 3 mL of sterile saline through a R ventricular puncture. All of the lung tissue is then harvested and prepared for the MPO assay. For this assay, lungs are individually homogenized in potassium phosphate buffer (pH 6.0 containing 0.5% hexadecyltrimethylammonium bromide). Following centrifugation (14,000×g, 10 min 4° C.) 50 μL of supernatant was added to 950 μL potassium phosphate buffer containing 0.2 mg/mL o-dianisidine dihydrochloride (Sigma-Aldrich) and 0.00002% hydrogen peroxide. Changes in absorbance are measured at 460 ηm. Cytokine levels are determined in BALF cell-free supernatant (200×g, 10 min, 4° C.) by ELISAs for TNFα, IL-6 (R&D Systems) using commercially available ELISAs. Particularly striking are the results for androst-5-ene-3β,7β,16α,17β-tetrol for which it was found that animals treated orally with this compound had reduced levels of MPO, TNFα and IL-6 in BAL as compared to vehicle treated animals. The effect on MPO, which is a measure of neutrophil burden in the lung, and the pro-inflammatory cytokine TNFα was particularly profound. This suggests the ability of the compound to block the migration of pro-inflammatory cells into inflamed tissue as well as to reduce the pro-inflammatory cytokine signaling. In this model, acute inflammation is presumably driven by LPS stimulation of elements of innate immunity. Many of these same mediators are increased and thought to be involved in lung inflammation associated with several disorders, including cystic fibrosis, chronic obstructive pulmonary diseases, acute and chronic bronchitis, and even certain infectious diseases like tuberculosis. The observation that treatment with androst-5-ene-3β,7β,16α,17β-tetrol dramatically reduced MPO and pro-inflammatory cytokine levels in BALF at 48 h is in keeping with the anti-inflammatory activities reported herein for androst-5-ene-3β,7β,16α,17β-tetrol in disease specific models of chronic inflammation, including EAE.

Example 10

Human mixed lymphocyte reaction (MLR). The capacity of Compound 1 to affect antigen specific stimulation in which human T lymphocytes respond to a specific foreign antigen (major histocompatibility complex) is studied. The MLR is typically used as an in vitro model of delayed type hypersensitivity responses and shows the effect that a compound can have on human antigen-specific T cell responses in vivo. Inhibition of the MLR by a compound shows an immune suppression effect of the compound on lymphocytes. Compounds that do not inhibit the MLR are not immune suppressive for the antigen specific activation of responding lymphocytes.

Blood samples are obtained from 3 (2 males, 1 female) fasting, healthy human volunteers of 23-31 years old. The subjects did not use immunomodulatory, anti-allergic drugs or antibiotics in the three months before the study. The subjects are bled between 9 and 10 AM to limit possible fluctuations in the circulating levels of hormones or cytokines that could have influenced the in vitro responses of their lymphocytes. Peripheral blood mononuclear cells (PBMC) are isolated by centrifugation on Ficoll-Hypaque (density 1.077, Biochrom AG, Berlin, Germany) gradients and resuspended in culture medium (RPMI 1640 supplemented with 2 mM L-glutamine, penicillin (100 U/mL) and streptomycin (100 mg/mL) (Invitrogen s.rl., Milan, Italy). Autologous (responder) inactivated plasma is used at 10%. Five hundred thousand responder PBMC (PBMCr) and 500,000 allogeneic irradiated (30 Gy) stimulator PBMC (PBMCs) are mixed at a ratio of 1:1 in 200 μL medium and cultured for 6 days in flat bottom 96 well plates (Nunc, Roskilde, Denmark) at a concentration of 300 nM or 30 nM for each of the test compounds. The test compounds, such as Compound 1, are dissolved in ethanol and then diluted to the desired concentration with culture medium leading to a final solution containing 0.01% of ethanol. This vehicle is used as control. Controls also include PBMCr and PBMCs cultured separately. During the last 8 hours of the culture period the PBMC are pulsed with 1 μCi/well [$^3$H] thymidine (Amersham, Milan, Italy). The cells were then harvested and radioactivity incorporation measured with a beta cell counter. The mean cpm of quadruplicate wells are calculated. Proliferation of T cells is expressed as a stimulation index: SI=cpm (PMBCs×PBMCr)/cpm (PBMCr)+cpm (PBMCs). Statistical analysis are performed using the Student's t test. The cpm to be obtained from quadruplicate of each test compound is compared to proliferative responses obtained in control PBMCr and PBMCs cultured in the presence of the vehicle. Differences are considered significant at p<0.05.

The results are consistent with the capacity of Compound 1 to be anti-inflammatory agents without being immune suppressive.

Example 11

Analysis of immune suppression. Glucocorticoid steroids such as dexamethasone or hydrocortisone are typically immune suppressive and have significant toxicities associated with their use. Immune suppression is examined in a reporter antigen popliteal lymph node assay in mice essentially as previously described (C. Goebel et al., *Inflamm. Res.*, 45(Suppl. 2):S85-S90,1996; R. Pieters et al., *Environmental Health Perspectives* 107(Suppl. 5):673-677, 1999). This protocol is used to analyze the activity of Compound 1 in the popliteal lymph node (PLN) assay to show that the compound does not have appreciable immune suppression activity in vivo. Assessment of activity includes (1) measuring suppression of numbers of total lymphocytes, antigen specific IgM, IgG1 and IgG2a antibody secreting cells (ASC) (ELISPOT assay) in popliteal lymph node cells; (2) analysis of cell surface marker (CD4, CD8, CD19, F480, CD80, CD86) expression by flow cytometry of living cells in suspension; and (3) IL-4, TNFα and IFNγ production by lymphocytes in vitro (ELISA).

Groups (n=5 per group) of specific pathogen free BALB/C mice are used. The Positive control group is treated with vehicle (oral gavage) and 5 µg/day dexamethasone by subcutaneous injection to induce immune suppression. Vehicle control animals (negative control) were treated with vehicle alone (oral gavage). One group of animals is treated with Compound 1 at 0.1 mg/day by oral gavage. Another group is treated with 1 mg/day of Compound 1. The results are analyzed by two-tailed Student's t-test with equal variance. The animals are injected in the right hind footpad with 50 µL of freshly prepared sensitizing dose of TNP-OVA. Dexamethasone (decadron phosphate injection; dexamethasone sodium phosphate) is administered by subcutaneous injection into the nape of the neck daily, immediately following sensitization with TNP-OVA. Compound 1 is given immediately afterwards by gavage. Five days after injection of TNP-OVA, blood is drawn by orbital puncture, and the mice are euthanized by cervical dislocation and popliteal lymph nodes are removed and separated from adherent fatty tissue. Single cell suspensions are prepared, resuspended in 1 mL PBS-BSA (1%) and counted. Cell numbers, IL-4, IL-5 and IFNγ were measured.

The average number of lymphocytes in PLNs from the vehicle control group is typically $7.8 \times 10^6$ per lymph node compared to $2.9 \times 10^6$ per lymph node in the dexamethasone treated animal group. Such reduced lymphocyte count clearly shows the marked immune suppression that is typically seen with the use of dexamethasone or other glucocorticoid compounds. The results show that Compound 1 is not immune suppressive. By contrast, IFNγ, IL-4 and IL-5 levels were reduced in the dexamethasone treated group compared to the vehicle control group or to either drug treated group.

Example 12

Glucose lowering and amelioration of insulin resistance. Glucose lowering effects and amelioration of insulin resistance is assessed in the diabetic db/db mouse model of human diabetes and insulin resistance. In these studies, db/db C57BUKs mice of approximately 8 to 10 weeks of age are divided into groups of 10 each and then treated with a vehicle control (no drug) or Compound 1 by oral gavage. The compound was administered twice a day at 20 mg/kg/day (10 mg/kg dose administered twice per day), 40 mg/kg/day (20 mg/kg dose administered twice per day) or 80 mg/kg/day (40 mg/kg dose administered twice per day) for up to 28 days. Blood glucose levels are monitored twice a week during the dosing period, using a minute amount of blood (nick tail bleeds) to measure the concentration of glucose by glucometer strips. At specific times during the dosing period (day 14 and day 28), an oral glucose tolerance test (OGTT) is also performed by administering a standard oral dose of 1 g/kg glucose (approximately 40 mg in a 40 mg mouse) and then the fluctuation of blood glucose levels is monitored quickly thereafter after at 15, 30, 60 and 120 minutes after the glucose dose. In the drug treated group, a decrease in hyperglycemic blood glucose levels is observed in the db/db mice.

Example 13

Diet induced obesity (DIO) mouse hyperglycemia treatment. The effect of a drug to enhance peripheral sensitivity to insulin can be studied in a mouse model in which a state of insulin resistance is attained by feeding the animals a fat-enriched diet (60% of total caloric intake) for at least 6 weeks. This model has been described, e.g., J. N. Thupari et al., *Proc. Natl. Acad. Sci. USA*, 99(14):9498-9502, 2002, H. Xu et al., *J. Clin. Invest.*, 112:1821-1830, 2003, H. Takahashi et al., *J. Biol. Chem.*, 278(47):46654-46660, 2003. Under these diet conditions, the mice exhibit increased body weight (+35 g) and a state of glucose intolerance, which is manifested as a significant delay in the clearance time of orally-administered glucose during a standard OGTT (oral glucose tolerance test).

For these studies, animals of approximately 4 weeks of age were divided into groups of 10 animals each and then are treated with a vehicle control (no drug) or Compound 1. In this DIO-model of insulin resistance, Compound 1 reduces glucose intolerance compared to vehicle control animals as indicated by significant improvement in the OGTT glycemic excursion. These findings shows that treatment with Compound 1 enhances peripheral insulin sensitivity or uptake, which improves glucose intolerance in these animals.

Example 14

A treatment protocol similar to that previously described (vide supra) is performed with db/db mice that were younger than the animals described in example 15. The animals (n=8 to 10 per group) are treated with Compound 1 or vehicle by oral gavage twice per day. At the start of dosing, the animals are about 6 weeks of age, before the onset of elevated glucose levels or hyperglycemia. Dosing with vehicle or drug is maintained for 32 days to determine the effect of the treatments on the onset and rate of progression of hyperglycemia in the animals. In the control group, the onset of hyperglycemia is observed after 25 days of dosing and it continued to worsen, i.e., blood glucose levels rise from normal to frank hyperglycemia, through the end of the 32 day dosing period. By contrast, levels of glucose in the drug treatment group does not rise above normal levels by the end of the 32 day dosing period, showing that drug treatment delayed the onset of hyperglycemia through the course of the protocol.

Administration of Compound 1 to 8 week old male diabetic db/db mice suppresses basal blood glucose hyperglycemic levels, an effect that typically becomes apparent after 10 days of dosing and is sustained for 18 additional days of continuous, twice-a-day treatment. In younger, 6 week old male db/db mice, treatment with Compound 1 blocks or retards progression of the animals into the hyperglycemic state that is observed in the vehicle-treated group after 25 days of dosing. The treated animals maintain blood glucose levels that were comparable to those from lean db/+littermates. Results from OGTTs performed in treated animals model show amelioration of glucose intolerance compared to vehicle control animals.

Example 15

Glucose lowering in 8 week old db/db diabetic mice. The hyperinsulinemic-euglycemic clamp protocol was conducted to measure insulin sensitivity in vivo. In this procedure, insulin was administered to raise the insulin concentration while glucose was infused to maintain euglycemia or a fixed, normal blood glucose level (about 180 mg/dL). The glucose infusion rate (GIR) needed to maintain euglycemia showed insulin action in these animals. The objective of this protocol was to investigate characterize the capacity of androst-5-ene-3β,7β,16α,17β-tetrol (i.e., Compound 1) and other compounds to ameliorate systemic insulin resistance and improve whole body glucose disposal in the hyperinsulinemic-euglycemic clamp model. The degree of skeletal muscle and hepatic insulin sensitivity and tissue specific glucose uptake were also assessed. The animals were dosed daily by oral gavage for 14 days. On Day 10 of treatment catheters were implanted in the carotid artery and jugular vein. On the day of the clamp (day 14) the compound was administered at 7:30 am.

Body weight and glucose concentration were assessed on day 0, 7 and day 14 of treatment. On day 14 a euglycemic hyperinsulinemic clamp was performed. Food was removed at 7:30 am at 10:30 a primed continuous infusion of [3-$^3$H]-glucose (0.05 μCi/min). A baseline blood sample was taken at 12:50 (−10 min) and at 1:00 (0 min) a euglycemic hyperinsulinemic clamp was initiated by administering 10 mU/kg/min of insulin. Glucose was infused at a variable rate to clamp the glucose concentration at ~180 mg/dl. A bolus of [$^{14}$C]-2deoxyglucose was given at the end of the study to assess tissue specific glucose uptake. Plasma $^{14}$C 2-deoxyglucose was assessed at 122, 125, 130, 135, 145 min. The animals were then anesthetized with an intravenous infusion of sodium-pentobarbital and selected tissues were removed, immediately frozen in liquid nitrogen and stored at −70° C. until analysis.

Analysis was conducted as follows. Plasma samples were deproteinized with Ba(OH)$_2$ (0.3 N) and ZnSO$_4$ (0.3 N), dried and radioactivity was assessed on scintillation counter (Packard TRICARB 2900 TR, Meriden, Conn.). Frozen tissue samples were homogenized in 0.5% perchloric acid, centrifuged and neutralized. One supernatant was directly counted to determine radioactivity from both [$_{14}$C] DG and [$^{14}$C] DGP. A second aliquot was treated with Ba(OH)$_2$ and ZnSO$_4$ to remove $^{14}$C DGP and any tracer incorporated into glycogen and then counted to determine radioactivity from free [$^{14}$C] DG(2). [$^{14}$C]DGP was calculated as the difference between the two aliquots. The accumulation of [$^{14}$C]DGP was normalized to tissue weight and tracer bolus. Rg, an index of tissue specific glucose uptake was calculated as previously described (E. W. Kraegen et al., *Am. J. Physiol.*, 248:E353-E362, 1985). Whole body glucose turnover was calculated as the ratio of the $^3$H glucose infusion rate (dpm/kg/min) and arterial plasma glucose specific activity (dpm/mg). Endogenous glucose production was calculated as the difference between the whole body glucose turnover and the exogenous glucose infusion rate (R. N. Bergman et al., *Endocr. Rev.*, 6:45-86, 1985). Treatment groups are summarized in the table shown below.

| Group | Treatment | Dosing volume and dosing solution concentration | N |
|---|---|---|---|
| A - vehicle control* | vehicle 8 mL/kg, po, bid for 13 days, qd on day 14 | 8 mL/kg | 10 |
| D - Compound 1** | 40 mg/kg, po, bid for 13 days, qd on day 14 | 4 mL/kg of 10 mg/mL in vehicle | 10 |
| E - positive*** control | 25 mg/kg, po, bid for 13 days, qd on day 14 | 5 mL/kg of 5 mg/mL in water + 1% CMC | 10 |

*vehicle: 30% sulfobutylether in water (20 mg/mL of drug in solution for groups B-D)
**Compound 1: androst-5-ene-3β,7β,16α,17β-tetrol
***rosiglitazone maleate (31493r, AApin Chemicals Limited (UK),
CMC—Carboxymethyl cellulose (medium grade, C4888, Sigma)

The insulin dose was 10 mU/kg/min. In a normal animal, this dose of insulin would require infusion of ~90 mg/kg/min of glucose to keep the glucose level clamped at ~150 mg/dl. The average glucose requirement in all treatment groups was ~50% of normal. The results showed that Compound 1 increased the glucose infusion rate compared to the vehicle control, which means insulin action was improved.

Using the 3-$^3$H glucose tracer, the rate of liver glucose production was calculated during the basal period and the ability of insulin to suppress liver glucose production during the clamp. In severe insulin resistant animals endogenous glucose production would decrease by about 50% with the insulin dose that was used. In groups D and E, insulin completely suppressed endogenous glucose production (p<0.05), which showed an improvement in hepatic insulin action.

To assess peripheral insulin action, tissue specific glucose uptake during the euglycemic hyperinsulinemic clamp was assessed using $^{14}$C-2-deoxyglucose. A bolus of $^{14}$C-2-deoxyglucose was given at 120 min. Tissues were collected 25 minutes later. Tissues were analyzed for total accumulation of $^{14}$C-2-deoxyglucose phosphate. In this protocol, brain glucose uptake is unaffected by most treatment regimens and it thus serves as an internal control. The results showed that brain glucose uptake was comparable between all of the groups. In the heart and diaphragm, glucose uptake was higher in the treated groups compared to the vehicle control group. Both androst-5-ene-3β,7β,16α,17β-tetrol and rosiglitazone were more effective (p<0.05) in augmenting muscle glucose uptake in the gastrocnemius muscle. In white vastus muscle, which is a non oxidative muscle group, differences were not detected except between androst-5-ene-3β,7β,16α,17β-tetrol and rosiglitazone.

Example 16

Rats are fed ad libum with a standard laboratory chow that contained Compound 1 for 6 days, followed by analysis of liver tissue on day 6 for levels of phosphoenolpyruvate carboxykinase ("PEPCK") and 11β-hydroxysteroid dehydrogenase ("11β-HSD") in the liver. Control animals are fed normal chow and livers are examined on day 6 for PEPCK and 11β-HSD levels by measurement of messenger RNAs (mRNAs) by RT-PCR. Both control and treated animals have free access to water. Administration of the compound in chow for 6 days is found to decrease levels of 11β-HSD type 1 ("11β-HSD1") and PEPCK in liver tissue as shown below. Levels of PPARα mRNA in these animals were not affected by feeding with androst-5-ene-3β,7β,17β-triol.

| | 11β-HSD1 mRNA | PEPCK mRNA | PPARα mRNA |
|---|---|---|---|
| control (no compound) | 100% | 100% | 100% |
| androst-5-ene-3β,7β,17β-triol | 45% | 30% | 105% |

In another study, administration of the Compound 1 to mice is found to decrease expression of 11β-HSD1 in osteoblasts by about 50%, which is consistent with the observation that the compound possesses bone-sparing effects in mice treated with dexamethasone, a glucocorticoid that induces bone loss in vivo.

In another study, total RNA from perigonadal fat tissue from lean db/+ or diabetic db/db mice treated with Compound 1 is isolated and processed for quantitative RT/PCR using primers specific for monocyte chemoattractant protein-1 (MCP-1) using an iCycler iQ multicolor real time-detection system (Bio-Rad). RNA expression levels are normalized with respect to the vehicle control. The compound is found to decrease levels of monocyte chemoattractant protein-1 (MCP-1) by about 50%. For this study, vehicle is also administered to a control group of age matched lean heterozygous db/+mice.

Example 17

Synthesis of compounds is described below.

Androst-5-ene-3β,7β,16α,17β-tetrol (7)

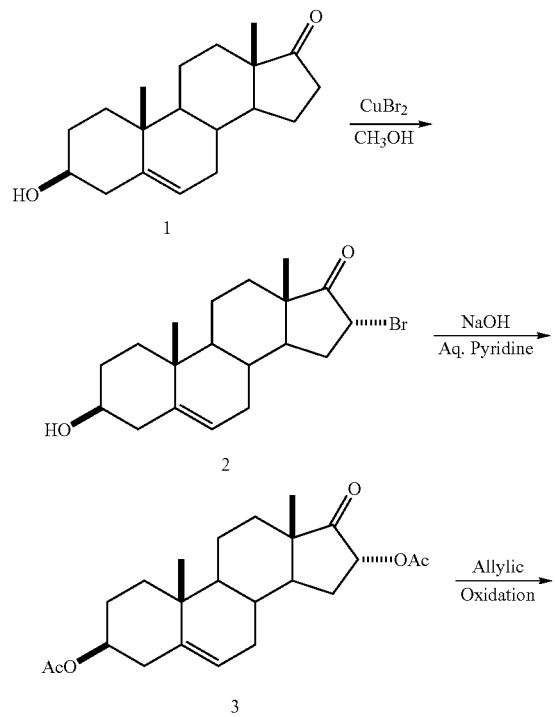

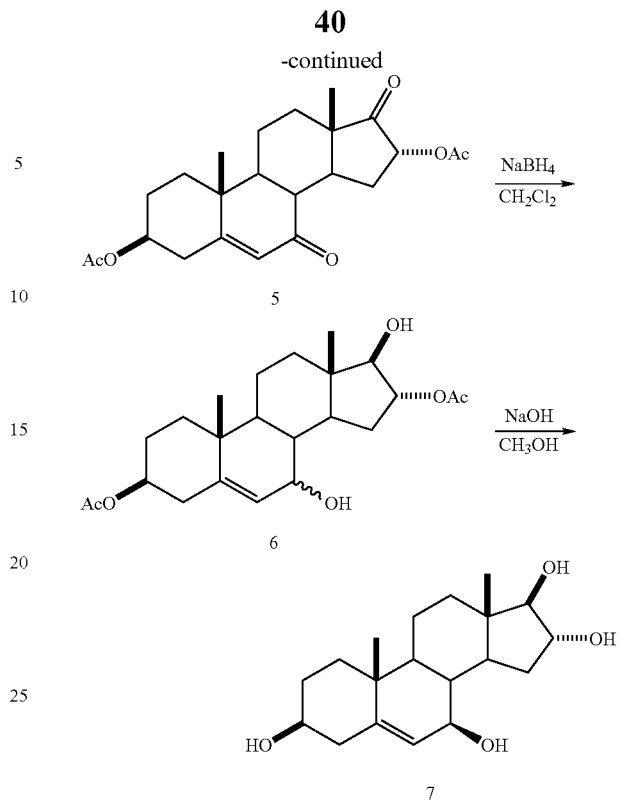

5-androstene-3β,16α-diol-17-one diacetate (3). 16α-bromodehydroepiandrosterone 2 was prepared by refluxing DHEA (1) in methanol with copper (II) bromide. To 15.0 g of 2 (40.8 mmol) in pyridine (129 mL) and water (309 mL) was added 120 mL of 1N aqueous sodium hydroxide and the mixture was stirred in air for 15 minutes. The reaction mixture was poured into ice/water saturated with sodium chloride and containing excess hydrochloric acid. The crude product was filtered, washed with water until neutral and dried in vacuo over anhydrous calcium chloride at 55-60° C. Recrystallization from methanol afforded 8.21 g of 16α-hydroxy-DHEA (Mp 194.4-195.1° C.). This product was then converted to the diacetate 3 by treatment with excess acetic acid in pyridine and purified by flash chromatography.

5-Androstene-3β,16α-diol-7,17-dione (5). To a solution of 3 (20.1 g, 51.7 mmol) in benzene containing celite (60 g) and pyridinium dichromate (75 g) was added 22 mL of 70% tert-butyl hydrogen peroxide. After 2 days of stirring at room temperature, diethyl ether (600 mL) was added and precipitate was filtered and washed with ether (2×100 mL). The residue was purified by flash chromatography (60% ethyl acetate in hexanes) and recrystallized to give 16.0 g (39.8 mmol, 77%) of 5 as prisms. Mp 205.6-206.2° C.

5-Androstene-3β,7β,16α,17β-tetrol (7). To a solution of 5 (10.0 g, 24.8 mmol) in dichloromethane (75 mL) and methanol (255 mL) at 0° C. was added 1.5 g of sodium borohydride and the mixture was stirred at 0° C. for 1 hour. After quenching with acetic acid (3.5 mL) the reaction mixture was partitioned between dichloromethane and water. The organic layer was concentrated to a mixture of 7α and 7β diacetate tetrols. This mixture was purified by flash chromatography and HPLC to give 2.90 g of the 7β-epimer (9.5 mmol, 38%). Mp 216.8-220.8° C. Saponification in methanol (100 mL) with 1N sodium hydroxide (60 mL) for 2 days at room temperature and purification by HPLC gave 7 (1.41 g, 4.4 mmol, 46%) as fine needles from aqueous acetonitrile. Mp 202.1-206.4° C.;

[a]D+1.35 (methanol, c=1). Selected $^1$H NMR peaks (CD$_3$OD): δ 0.77 (s, 3H), 1.01 (s, 3H), 3.39 (d, 1H), 3.46 (m, 1H), 3.74 (t, 1H), 4.04 (m, 1H), 5.55 (dd, 1H).

Example 18

Treatment of gastrointestinal inflammation. The capacity of Compound 1 to limit or inhibit inflammation or symptoms of inflammation is shown using an animal model for inflammatory bowel disease using the following protocol.

Groups of 3 male Wistar rats (180±20 grams) fasted for 24 hours before 2,4-dinitrobenzene sulfonic acid (DNBS) or saline challenge are used. Distal colitis is induced by intracolonic instillation of 0.5 mL of an ethanolic solution of DNBS (30 mg in 0.5 mL of a 30% ethanol in saline solution) after which 2 mL of air was injected through the cannula to ensure that the solution remained in the colon. The volume used was 0.1 mL per injection of 2 and 20 mg/mL of compound such as androst-5-ene-3β,7β,17β-triol or Compound 1 in a liquid formulation, which was administered by subcutaneous injection once a day for 6 days (0.2 mg/animal/day or 2.0 mg/animal/day). The formulation contains 100 mg/mL of compound. Concentrations of 2 mg/mL and 20 mg/mL are obtained by diluting the 20 mg/mL formulation with vehicle that lacked compound.

The first dose is given 30 minutes after DNBS challenge. Sulfasalazine (30 mg/mL in 2% Tween 80 in distilled water) was administered orally (PO) once a day (10 mL/kg/day) for 7 days, the first two doses beginning 24 hours and 2 hours before DNBS challenge. The presence of diarrhea is recorded daily by examining the anal area. Animals are fasted for 24 hours prior to being sacrificed. Animals are sacrificed on day 7 or day 8 and their colons are removed and weighed. Before removal of the colon, signs of adhesion between the colon and other organs are recorded. Also, the presence of ulcerations is noted after weighing of each colon. The "net" change of colon-to-body weight (BW) ratio is normalized relative to saline-challenged baseline group. A 25-30% decrease in "net" colon-to-body weight ratio is considered significant. The results showed that androst-5-ene-3β,7β,17β-triol had a modest effect on the course of disease (about 15-20% decrease in net colon-to-body weight ratio), while treatments with androst-5-ene-3β,7β,16α,17β-tetrol is effective (about 25-35% decrease in net colon-to-body weight ratio).

Variations of this protocol include administration of compounds in an aqueous solution with or without 30% sulfobutylether-cyclodextrin in water using dose levels described above and/or one or more of 0.05 mg/animal/day, 0.1 mg/animal/day, 0.5 mg/animal/day and 1.0 mg/animal/day.

Example 19

The capacity of 5-androstene-3β,7β,17β-triol, Compound 1 and other compounds to reverse adverse effects of glucocorticoids in bone growth was shown in the human MG-63 osteosarcoma cell line. MG-63 cells are osteoblasts, which are cells that mediate bone growth. Theis cell line has been used extensively to study bone biology and to characterize the biological activity of compounds for treatment of bone loss conditions (e.g., B. D. Boyan et al., *J. Biol. Chem.*, 264(20): 11879-11886, 1989; L. C. Hofbauer et al., *Endocrinology*, 140(10):4382-4389,1999). Adverse toxicities associated with elevated glucocorticoid levels include a decrease in the production of IL-6 and IL-8 by osteoblasts, including the MG-63 cell line, and an increase in the expression of the 11β-hydroxysteroid dehydrogenase type 1 enzyme (11β-HSD). Increased 11β-hydroxysteroid dehydrogenase type 1 enzyme results in increased levels of endogenous glucocorticoid activity by converting endogenous cortisone to the active cortisol, which inhibits bone growth. The 11β-HSD enzyme is expressed in liver, adipose tissue, brain and bone tissues. Cortisol generated by 11β-HSD-1 contributes to osteoporosis, insulin resistance, type 2 diabetes, dyslipidemia, obesity, central nervous system disorders such as stroke, neuron death, depression and Parkinson Disease. Decreases in IL-6, IL-8 and osteoprotegerin are associated with decreased bone growth by osteoblasts. Pilot studies showed that the IC$_{50}$ for inhibition of IL-6 from MG-63 cells by dexamethasone was 10 nM and the IC$_{50}$ for inhibition of growth of MG-63 cells by dexamethasone was 15.3 nM. In this protocol, MG-63 cells are grown in the presence or absence of the synthetic glucocorticoid dexamethasone at a 30 nM concentration and in the presence or absence of test compound.

These results showed that the test compounds at 10 nM partially reversed the adverse effects of dexamethasone at 30 nM, which shows that the compounds can reverse multiple toxicities associated with elevated glucocorticoid levels in osteoblasts, which are the cells that mediate bone growth. Osteoprotegerin is a factor associated with bone growth and decreased osteoprotegerin synthesis is associated with bone loss. Compound 1 completely or partially reversed the decrease in osteoprotegerin synthesis by MG-63 cells in the presence of 30 nM dexamethasone (normal osteoprotegerin levels at 0.1 µM).

To show that relevant effects could be obtained in vivo, Compound 1 is administered to mice that were also treated daily with dexamethasone for 23 days to reduce levels of osteoprotegerin in the animals. Osteoprotegerin levels in mice that are treated with vehicle and dexamethasone at 10 µg/day (positive control group) typically show 3.3 pMol/L osteoprotegerin, The degree of apoptosis of osteoblasts and osteocytes in murine vertebral bone as a function of estrogen deficiency was examined. Swiss Webster mice (four months old) were ovariectomized. Twenty-eight days later, the animals were sacrificed, vertebrae were isolated, fixed and embedded, and then undecalcified in methacrylate. The prevalence of osteoblast and osteocyte apoptosis was determined by the TUNEL method with CuSO$_4$ enhancement, and was found to be increased following loss of estrogen.

Collectively, the results described in this example are evidence that compounds such as Compound 1 affect bone tissue by both increasing bone growth and by inhibiting bone loss. Compound 1 does not interact with androgen receptor, estrogen receptor-α or estrogen receptor-β, which is consistent with their capacity to treat bone loss conditions without exerting unwanted sex hormone activity.

Example 20

Metabolic stability. The metabolic stability of selected compounds including Compound 1 was examined in vitro using microsomes obtained from liver tissue according to the following protocol. Microsomes in this protocol are capable of hydroxylation reactions and redox reactions that interconvert hydroxyl and ketones on the steroid molecules. Microsomes do not mediate conjugation reactions, e.g., sulfation of 30-hydroxyl groups or glucuronidation of 3α-hydroxyl groups.

The protocol was performed as follows. (1) Prepared 0.5 mM compound in acetonitrile/water 35:65. For androst-5-ene-30,170-diol, prepared 0.145 mg/mL, or 29.0 µL of a 1 mg/mL stock plus 171 µL solvent. For the standard curve dilutions of the 0.5 mM stock was used to obtain final concentrations of androst-5-ene-3β,17β-diol at 10 μM, 5 μM and 1 μM. (2) Set up samples as follows. Each assay consisted of an androst-5-ene-3β,17β-diol control and 1-8 unknown compounds. Tubes for each compound was follows: 1-0'2-0'3-0'4-0'*5-0'*6-5 μM 7-1 μM 8-30'9-30'10-30' where * designated denatured microsome negative control reaction tubes. For additional compounds numbering was started at 11, 21, 31, etc. (3) Added 315 μL PBS (pH 7.3-7.5) to each tube. Added 10 μL of the appropriate test article solution to each tube. (4) The internal standard/acetonitrile solution. (5) The NADPH regenerating system (NRS) was 125 μL per tube. To PBS added 1.7 mg/ml NADP, 7.8 mg/ml glucose-6-phosphate, 6 units/mL glucose-6-phosphate dehydrogenase. Fresh NRS for each experiment was kept on ice until use. (6) Each reaction used 125 μL of NRS in each tube. (7) Removed liver microsome preparation from −80° C. freezer and thawed in a room temperature water bath. The microsomal preparation was at a concentration of 20 mg/ml. Each reaction used 0.25 mg/tube and was diluted to a concentration of 5 mg/ml in PBS (i.e. 4-fold dilution) and kept on ice. (8) For the zero-time and denatured microsome control tubes 500 μL acetonitrile at −20° C. was added. Zero time tubes were transferred to ice and denatured microsome controls were preincubated at 37° C. for 5 minutes. (9) Assay tubes containing the microsomal preparation was also preincubated for 5 min at 37° C. (10) For each incubation tube, the reaction was started by addition of 50 μL of the microsome preparation and vortexing to mix. (11) Each reaction was terminated by adding 500 μL acetonitrile at −20° C. and vortexing. (12) After the reaction was terminated, 100 μL from each reaction tube was transferred to a fresh tube and 200 μL of water and 1400 μL of methyl-t-butyl ether was added to each tube. The tubes were Vortexed and centrifuged at 13,000 rpm for 10 min on a microfuge. The tubes were then put on a dry ice-methanol bath until aqueous layer was frozen solid. (13) The methyl-t-butyl ether was transferred from each tube to a fresh tube and the solvent was evaporated ether under nitrogen and the precipitate was then resuspended in 10 μL acetonitrile/water 35:65 and analyzed by LCMS. Results are shown in the table below for the incubation times shown below.

| Compound | parent remaining human microsomes | parent remaining mouse microsomes |
|---|---|---|
| androst-5-ene-3β,17β-diol | 39% (10 min) | 25% (10 min) |
| androst-5-ene-3β,17β-diol | 30% (90 min) | — |
| androst-5-ene-3β,7β,17β-triol | 86% (90 min) | 89% (10 min) |
| androst-5-ene-3β,7β,16α,17β-tetrol | 100% (10 min) | 100% (10 min) |

*rat microsome instead of mouse preparation

The results show that Compound 1 is resistant to redox reactions, which is consistent with a greatly reduced degree of metabolism compared to the androst-5-ene-3β,17β-diol reference compound. This observation was quite unexpected because each of the four hydroxyl groups could potentially be reduced to a ketone, but none was in fact affected.

Example 21

Measurement of drug absorption with CaCo-2 cells. This protocol was used to measure the influx of compounds across a CaCo-2 cell monolayer. CaCo-2 cells are human cells with a polarized, highly differentiated cell line demonstrating an intestinal absorptive cell phenotype (J. Hunter et al., *J. Biol. Chem.*, 268(20):14991-14997,1993). This cell line is used to study the rate at which various compounds cross the cell monolayer. Typically, confluent monolayers of Caco-2 cells are used to model the intestinal epithelium and to obtain permeability coefficients from the steady-state flux of test compounds. This can provide information about a compound's potential to be orally bioavailable.

In this protocol, the cells were maintained in medium at 37° C., using 100 μL per well of warm medium in a sterile 50 ml tube. The cells were grown on sterile 24-well plates with 600 μL of differentiation medium per well. The wells contained a transwell insert to allow two compartments per well. 100 μL of differentiation medium was carefully added into each well, touching the pipette tip to the side of well. Cells were incubated at 37° C., 5% $CO_2$, saturating humidity for 48 hours to form a monolayer. For each plate, tubes were numbered with tubes 1-24 for basolateral buffer to serve as a basolateral zero time point ($T_0$). Tubes 26 to 49 were apical buffer containing test article to serve as apical $T_0$. Tubes 51-74 were the $T_{20}$ time point (20 minute), 76-99 were the $T_{40}$ time point, 101-124 were the $T_{80}$ time point, 126-149 were the $T_{120}$ time point, and 151-174 were $T_{120}$ apical samples for mass balance determination. Tubes 175-179 were the 5-point standard curve for Compound 1, tubes 180-184 were the standard curve for Compound 2 and so on to tubes 230-234 for Compound 12. Tubes 1-49 were placed in 4 rows in rack 1, 51-99 in rack 2, 101-149 in rack 3, 151-174 in rack 4, and 175-234 in racks 5 and 6.

Buffers were prepared by removing 150 mL of transport buffer from a fresh 1000 mL bottle (at pH to 7.4 with 1 N HCl). This buffer is 'basolateral'. The pH of the remaining 850 mL was adjusted to 6.5 with 1 N HCL for the 'apical' buffer. 150 mL of apical buffer was placed in a separate vessel, and the remaining 700 mL was used the for rinsing. Buffers were stored at 4° C. but used at room temperature for the protocol.

After differentiation medium reached room temperature, about 20 mL was poured into a small beaker. The probe was equilibrated in this medium for 15 min. 24-well plates were removed from the incubator and allowed to reach room temperature. Each well was measured by the probe by inserting the probe into the well without touching the cell monolayer; press the TEST button when the probe is close to the medium surface and the reading will go from 0000 to a number when the probe touches the surface; a reading >1000Ω was acceptable. The apical buffer was then decanted from the transwell insert and the entire plate was rinsed in a 1000 mL beaker containing rinse buffer to remove all differentiating buffer. The transwells were then placed into the T20 plates. 10 μM of test compound and controls (carabamazapine MW 236; hydrochlorothiazide MW 351) was added in apical buffer by adding 0.1 μmol (e.g. 29 μl of a 1 mg/ml androst-5-ene-3β, 17β-diol reference solution) to 10 mL of apical buffer. 0.6 mL of basolateral buffer was then added to all wells.

A solution of 50 μg/ml 3α,7β,16α,17β-tetrahydroxyandrost-5-ene as an internal standard was made by adding 150 μL of the compound (1 mg/mL in ethanol) to 10 mL acetonitrile/water (25:75). Standard curves were made in basolateral buffer for each compound. The 10 μM apical buffer was diluted six fold when passing into the basolateral compartment, so the standard curve was prepared at a six fold lower concentration.

| Concentration | Apical TA (10 µM) | Baso Buffer |
| --- | --- | --- |
| 2 µM | 120 | 480 |
| 1 µM | 60 | 540 |
| 0.5 µM | 30 | 570 |
| 0.2 µM | 12 | 588 |
| 0.05 | 3 | 597 |

600 µL of basolateral buffer was placed in tubes 1-24 for the $T_o$ controls. 100 µL of apical buffer plus test article plus 500 µl apical buffer (so that concentration will be in standard curve range) was added to tubes 26-49 to serve as apical $T_o$. Place 100 µl apical buffer plus compound on the apical side. The time that the transwell was placed in the plate was taken as time zero ($T_o$). At T=20, the transwells were moved to the T40 plate and 600 µL of sample from the T20 plate was added to the appropriate tube. At T=40, the transwell was moved to the T80 plate and 600 µl of sample was taken from the T40 plate to the appropriate tube. At T=80, move the transwell to the T120 plate. Pipette 600 µl of sample from the T80 plate to the appropriate tube and so on for the remaining time points. 100 µL of the apical buffer was added to the appropriate tube for mass balance. Samples will immediately extracted immediately were placed in a freezer.

300 µL of each sample was transferred from the assay tube into a labeled 2 mL tube, except for tubes 151-174 (which contained only 100 µL); 50 µl of these samples were transferred and added to 250 µL of basolateral buffer (resulting in a 6-fold dilution). 20 µL of the 3α,7β,16α,17β-tetrahydroxyandrost-5-ene internal standard was added to each tube and 1500 µL of methyl-t-butyl ether was added to each tube. The tubes were vortexed, centrifuged in a microcentrifuge for 10 min. and placed in methanol/dry ice bath until frozen. Fresh tubes were labeled and the methyl-t-butyl ether was decanted from each frozen tube into the fresh tube. The methyl-t-butyl ether was then evaporated under nitrogen and reconstituted in 120 µL acetonitrile/water (35:65) and analyzed by LCMS. In the table below compound 1 was 3β,7β,16α,17β-tetrahydroxyandrost-5-ene

| Compound | Conc. (µM) apical @ $T_0$ | Cumulative basolateral conc. (µM) in 80 min | % apical transported in 80 min | Total % transported |
| --- | --- | --- | --- | --- |
| 1 | 2.195 | 0.017 | 0.008 | 0.8% |

Studies with the CaCo-2 cell line indicated that tetrol compounds such as androst-5-ene-3β,7β,16α,17β-tetrol were not highly permeable and would thus not be expected to be orally bioavailable. Despite that, the compound androst-5-ene-3β,7β,16α,17β-tetrol was active as described above when administered orally to mice in a diabetes treatment model. Other protocols showed that the degree of sulfation and the degree of glucuronidation for the tetrol compounds such as 3β,7β,16α,17β-tetrahydroxyandrost-5-ene was low compared to diols. This activity may have arisen at least partly from the low metabolism of tetrol compounds in vivo.

Example 22

Characterization of Solid State Forms

Raman Spectroscopy.

FT-Raman spectra were acquired on a Raman accessory module interfaced to a MAGNA 860™ Fourier transform infrared (FT-IR) spectrometer (Thermo Nicolet). The module uses an excitation wavelength of 1064 nm and an indium gallium arsenide (InGaAs) detector. Approximately 1.5 W of Nd:YVO$_4$ laser power was used to irradiate the sample. A total of 256 sample scans were collected from 3600-100 cm$^{-1}$ at a spectral resolution of 4 cm$^{-1}$ using Happ-Genzel apodization. Wavelength calibration was preformed using sulfur and cyclohexane. The Raman FT-IR spectrum of the solid state form of androst-5-ene-3β,7β,16α,17β-tetrol prepared according to Example 17 is presented in FIG. 1.

X-Ray Powder Diffraction.

XRPD patterns were collected using an Intel XRG-3000 diffractometer equipped with a curved position sensitive detector with a 2-theta range of 120° C. An incident beam of Cu Kα radiation (40 kV, 30 mA) was used to collect data in real time at a resolution of 0.03° 2-theta. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 µm, and the samples were analyzed for 5 minutes.

Figure 2:
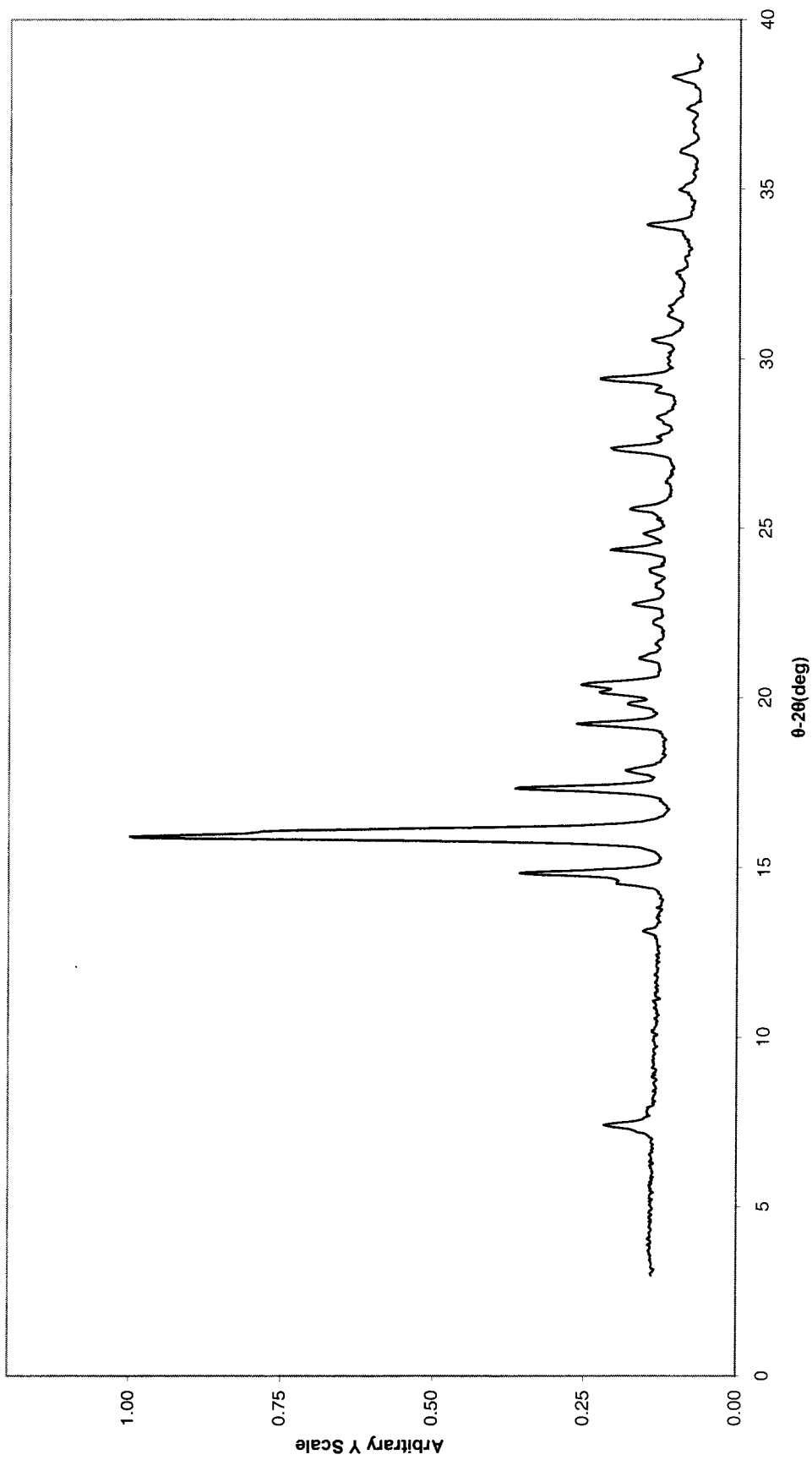
Figure 3:
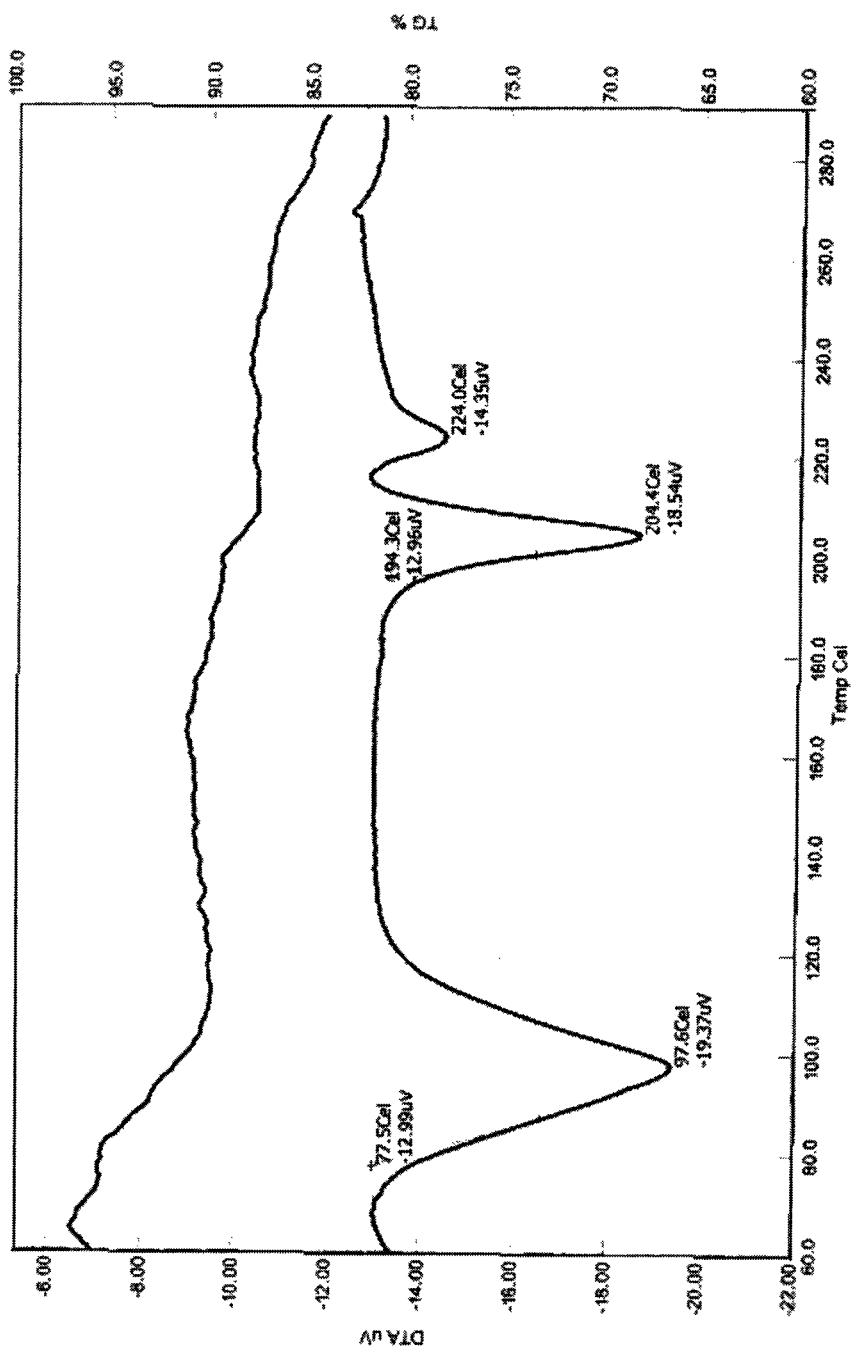

The Raman FT-IR spectrum of the solid state form of androst-5-ene-3β,7β,16α,17β-tetrol prepared according to Example 17 is presented in FIG. 2 with the data tabulated in the following Table

| 2-Theta | d space (angstroms) | Intensity (%) |
| --- | --- | --- |
| 7.4 | 11.930 | 10 |
| 10.2 | 8.698 | 1 |
| 13.1 | 6.753 | 4 |
| 14.5 | 6.101 | 9 |
| 14.8 | 5.978 | 27 |
| 15.9 | 5.574 | 100 |
| 17.3 | 5.123 | 28 |
| 17.8 | 4.969 | 8 |
| 19.2 | 4.616 | 17 |
| 19.8 | 4.477 | 7 |
| 20.2 | 4.405 | 12 |
| 20.4 | 4.360 | 16 |
| 22.2 | 4.004 | 2 |
| 22.7 | 3.911 | 6 |
| 23.2 | 3.826 | 2 |
| 23.8 | 3.740 | 3 |
| 24.4 | 3.654 | 11 |
| 24.8 | 3.584 | 5 |
| 25.6 | 3.485 | 8 |
| 26.4 | 3.380 | 1 |
| 27.4 | 3.260 | 12 |
| 27.7 | 3.222 | 3 |
| 28.3 | 3.155 | 4 |
| 29.0 | 3.075 | 4 |
| 29.4 | 3.038 | 15 |

Differential Thermal and Thermogravimetric Analyses.

Thermal data was obtained on a Seiko TG/DTA 220U instrument. A 5-8 mg sample of Compound 1 in solid state form prepared according to Example 17 was loaded into an aluminum sample pan and tapped down with a glass rod. The sample, in the aluminum sample pan that was uncovered and uncrimped, was equilibrated at 25° C. and heated under nitrogen purge in at a rate of 10° C./minute to a final temperature of 300° C.

What is claimed is:

1. A product wherein the product is a solid state form of androst-5-ene-3β,7β,16α,17β-tetrol obtained by the process comprising (1) obtaining purified androst-5-ene-3β,7β,16α,17β-tetrol, and (2) recovering androst-5-ene-3β,7β,16α,17β-tetrol from aqueous acetonitrile.

2. The product of claim 1 characterized by:
(a) an X-ray powder pattern with 2-theta values of about 15.9, 17.3 and 19.2 and optionally one or more 2-theta values of about 7.4, 14.8, 20.4, 24.4, 27.4 and 29.4 and (b) with differential thermal analysis spectrum with a heating rate of 10° C./min having an endothermic transition centered at about 204° C. (onset at about 194° C.) optionally with an endotherm transition centered at about 98° C. or 224° C.

3. The product of claim 1 characterized by
(a) an X-ray powder pattern with 2-theta values of about 15.9, 17.3 and 19.2 and optionally one or more 2-theta values of about 7.4, 14.8, 20.4, 24.4, 27.4 and 29.4 and (b) a solid state infrared Raman spectrum with peaks at about 1670 cm$^{-1}$, 1462 cm$^{-1}$ and 1439 cm$^{-1}$.

4. A composition comprising one or more excipients and a solid state form of androst-5-ene-3β,7β,16α,17β-tetrol obtained by the process comprising (1) obtaining purified androst-5-ene-3β,7β,16α,17β-tetrol, and (2) recovering androst-5-ene-3β,7β,16α,17β-tetrol from aqueous acetonitrile.

5. A method of preparing a liquid formulation comprising admixing a solid state form of androst-5-ene-3β,7β,16α,17β-tetrol, obtained by the process comprising (1) obtaining purified androst-5-ene-3β,7β,16α,17β-tetrol, and (2) recovering androst-5-ene-3β,7β,16α,17β-tetrol from aqueous acetonitrile, with a liquid excipient.

6. A method of treating an inflammation condition or disease comprising administering an effective amount of a solid formulation to a subject in need thereof wherein the formulation comprises a solid state form of androst-5-ene-3β,7β,16α,17β-tetrol obtained by the steps (1) obtaining purified androst-5-ene-3β,7β,16α,17β-tetrol, and (2) recovering androst-5-ene-3β,7β,16α,17β-tetrol from aqueous acetonitrile.

7. The method of claim 6 wherein the inflammation condition or disease is a chronic, non-production inflammation condition or disease.

8. The method of claim 6 wherein the condition or disease is an autoimmune condition or disease.

9. The method of claim 6 wherein the condition or disease is a metabolic condition or disease.

10. The disease of claim 8 wherein the autoimmune disease is Type 1 diabetes.

11. The method of claim 9 wherein the metabolic condition is hyperglycemia.

* * * * *